(12) United States Patent
Kim et al.

(10) Patent No.: US 10,898,152 B1
(45) Date of Patent: Jan. 26, 2021

(54) STROKE DIAGNOSIS APPARATUS BASED ON ARTIFICIAL INTELLIGENCE AND METHOD

(71) Applicant: Heuron Co., Ltd., Incheon (KR)

(72) Inventors: Dohyun Kim, Suwon-si (KR); Soo Hwa Song, Uijeongbu-si (KR); Sumin Jung, Gwangju-si (KR); Jin Soo Lee, Seoul (KR); Seong Joon Lee, Seoul (KR)

(73) Assignee: Heuron Co., Ltd., Incheon (KR)

( * ) Notice: Subject to any disclaimer, the term of this patent is extended or adjusted under 35 U.S.C. 154(b) by 0 days.

(21) Appl. No.: 16/986,494

(22) Filed: Aug. 6, 2020

(30) Foreign Application Priority Data

May 21, 2020 (KR) ........................ 10-2020-0061088

(51) Int. Cl.
| | |
|---|---|
| *A61B 6/00* | (2006.01) |
| *G06T 7/11* | (2017.01) |
| *G06T 5/00* | (2006.01) |
| *G06T 7/174* | (2017.01) |
| *A61B 6/03* | (2006.01) |
| *G06T 7/00* | (2017.01) |

(52) U.S. Cl.
CPC ............ *A61B 6/5217* (2013.01); *A61B 6/032* (2013.01); *A61B 6/501* (2013.01); *A61B 6/507* (2013.01); *A61B 6/5258* (2013.01); *A61B 6/5294* (2013.01); *G06T 5/002* (2013.01); *G06T 7/0012* (2013.01); *G06T 7/11* (2017.01);
(Continued)

(58) Field of Classification Search
CPC ......... A61B 6/032; A61B 6/501; A61B 6/507; A61B 6/5217; A61B 6/5258; A61B 6/5294; G06T 5/002; G06T 7/0012; G06T 7/11; G06T 7/174; G06T 2207/10081;
(Continued)

(56) References Cited

U.S. PATENT DOCUMENTS

| | | | | |
|---|---|---|---|---|
| 2018/0025255 | A1* | 1/2018 | Poole | G06T 7/0014 |
| | | | | 382/131 |
| 2018/0365828 | A1* | 12/2018 | Mansi | G16H 50/20 |

(Continued)

FOREIGN PATENT DOCUMENTS

| | | |
|---|---|---|
| JP | 2005-131011 | 5/2005 |
| KR | 10-1540254 B1 | 7/2015 |

(Continued)

OTHER PUBLICATIONS

Chang et al. "Hybrid 3D/2D convolutional neural network for hemorrhage evaluation on head CT." American Journal of Neuroradiology 39.9 (2018): 1609-1616. (Year: 2018).*

(Continued)

*Primary Examiner* — Katrina R Fujita
(74) *Attorney, Agent, or Firm* — Sughrue Mion, PLLC

(57) ABSTRACT

Provided is a stroke diagnosis apparatus based on AI that includes: an image obtainer obtaining a non-contrast CT image related to the brain of at least one patient; a preprocessor pre-processing the non-contrast CT image and determining whether the at least one patient is in a non-hemorrhage state or a hemorrhage state on the basis of the pre-processed image; an image processor normalizing the pre-processed image and dividing and extracting an ROI (Region of Interest) using a preset standard mask template; and a determiner determining whether there is a problem with a cerebral large vessel of the at least one patient using the divided and extracted ROI.

26 Claims, 16 Drawing Sheets

(52) U.S. Cl.
CPC .... *G06T 7/174* (2017.01); *G06T 2207/10081* (2013.01); *G06T 2207/20081* (2013.01); *G06T 2207/20084* (2013.01); *G06T 2207/30016* (2013.01); *G06T 2207/30101* (2013.01)

(58) Field of Classification Search
CPC . G06T 2207/20081; G06T 2207/20084; G06T 2207/30016; G06T 2207/30101
See application file for complete search history.

(56) References Cited

U.S. PATENT DOCUMENTS

| | | | | |
|---|---|---|---|---|
| 2020/0090331 | A1* | 3/2020 | Mansi | G16H 80/00 |
| 2020/0311911 | A1* | 10/2020 | Poole | G16H 50/20 |
| 2020/0315455 | A1* | 10/2020 | Lee | A61B 5/0042 |

FOREIGN PATENT DOCUMENTS

| | | |
|---|---|---|
| KR | 10-2016-0082950 | 7/2016 |
| KR | 10-1754291 B1 | 7/2017 |
| KR | 10-2018-0034818 | 4/2018 |
| KR | 10-1860566 B1 | 5/2018 |
| KR | 10-1992057 B1 | 6/2019 |
| KR | 10-2058884 B1 | 12/2019 |
| KR | 10-2020-0007244 | 1/2020 |
| KR | 10-2068836 B1 | 2/2020 |
| KR | 10-2020-0064818 | 6/2020 |

OTHER PUBLICATIONS

Daykin et al. "Evaluation of an Automatic ASPECT Scoring System for Acute Stroke in Non-Contrast CT." Annual Conference on Medical Image Understanding and Analysis. Springer, Cham, 2017. (Year: 2017).*

Jung et al. "Evaluating a Deep-Learning System for Automatically Calculating the Stroke ASPECT Score." 2018 International Conference on Information and Communication Technology Convergence (ICTC). IEEE, 2018. (Year: 2018).*

Kuang et al. "Automated ASPECTS on noncontrast CT scans in patients with acute ischemic stroke using machine learning." American Journal of Neuroradiology 40.1 (Jan. 2019): 33-38. (Year: 2019).*

Mikhail et al. "Computational Image Analysis of Nonenhanced Computed Tomography for Acute Ischaemic Stroke: A Systematic Review." Journal of Stroke and Cerebrovascular Diseases (May 5, 2020): 104715. (Year: 2020).*

Öman et al. "3D convolutional neural networks applied to CT angiography in the detection of acute ischemic stroke." European radiology experimental 3.1 (Feb. 2019): 8. (Year: 2019).*

Patel et al. "intracerebral Haemorrhage Segmentation in noncontrast ct." Scientific reports 9.1 (Nov. 2019): 1-11. (Year: 2019).*

Takahashi et al. "Computerized identification of early ischemic changes in acute stroke in noncontrast CT using deep learning." Medical Imaging 2019: Computer-Aided Diagnosis. vol. 10950. International Society for Optics and Photonics, Mar. 2019. (Year: 2019).*

You et al. "Automated segmentation for hyperdense middle cerebral artery sign of acute ischemic stroke on non-contrast ct images." arXiv preprint arXiv:1905.09049 (May 22, 2019). (Year: 2019).*

Philip A Barber, et al., "Validity and reliability of a quantitative computed tomography score in predicting outcome of hyperacute stroke before thrombolytic therapy", ASPECTS Study Group-Alberta Stroke Programme Early CT Score, The Lancet, May 13, 2000, vol. 355, pp. 1670-1674.

Korean Patent Office, Notice of Allowance dated Sep. 28, 2020 in counterpart Korean Application No. 10-2020-0061088.

* cited by examiner

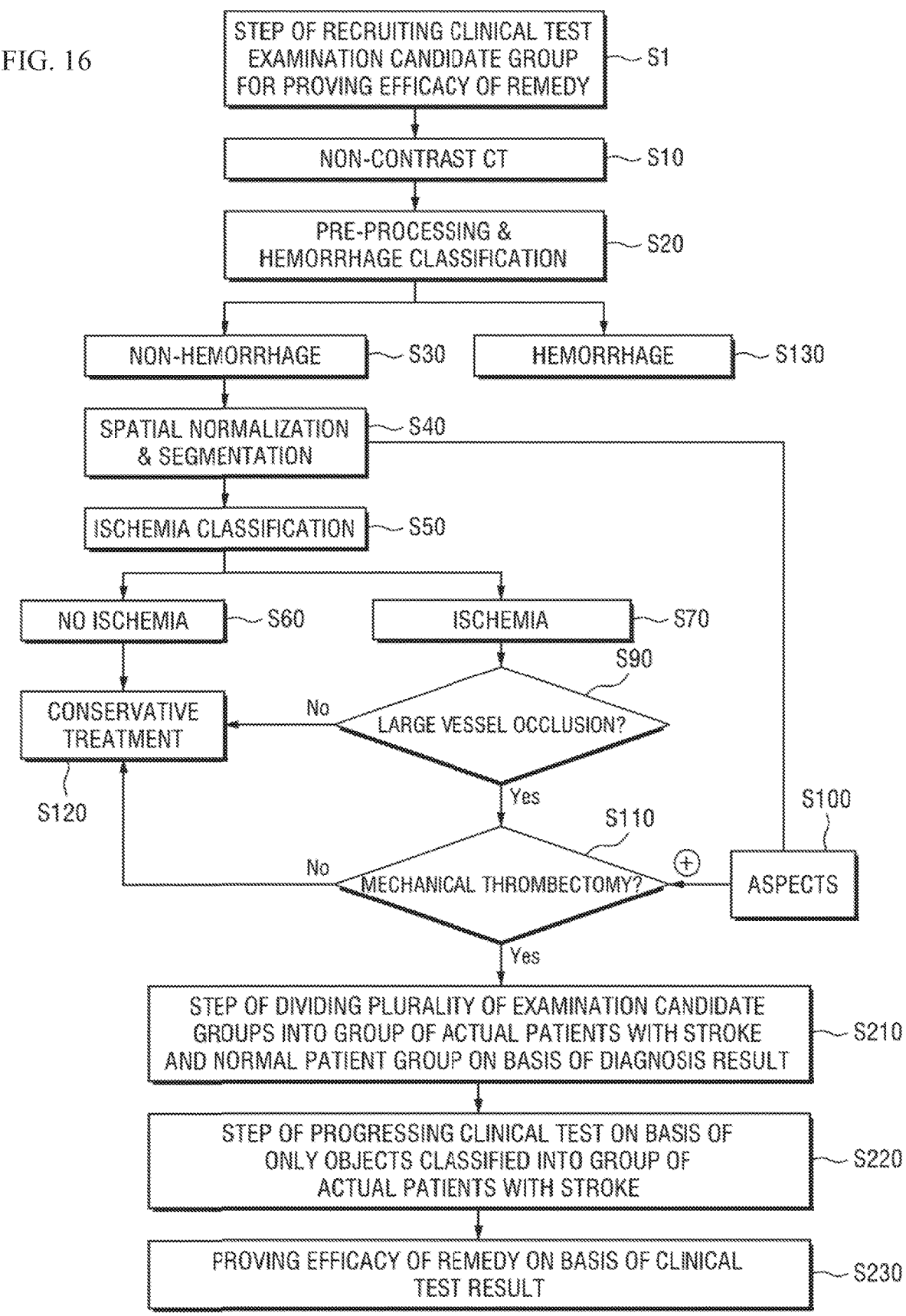

STROKE DIAGNOSIS APPARATUS BASED ON ARTIFICIAL INTELLIGENCE AND METHOD

CROSS-REFERENCE TO RELATED APPLICATIONS

This application claims the priority of Korean Patent Application No. 10-2020-0061088 filed on May 21, 2020, in the Korean Intellectual Property Office, the disclosure of which is incorporated herein by reference.

BACKGROUND

Field

The present disclosure relates to a stroke diagnosis apparatus and method based on AI (Artificial Intelligence). In more detail, the present disclosure relates to a stroke diagnosis apparatus and method using an AI algorithm that can classify a patient with a stroke and discriminate a patient with emergent large vessel occlusion on the basis of a non-contrast CT image.

Description of the Related Art

Brain diseases, that is, cerebrovascular diseases are classified into cerebral hemorrhage in which a cerebral vessel explodes, cerebral infarction in which a cerebral vessel is clogged with thrombosis, etc., cerebral aneurysm in which a cerebral vessel abnormally inflates, etc., and cerebral hemorrhage and cerebral infarction are generally called a 'stroke'.

In order to diagnose such brain diseases, non-invasive techniques such as ultrasonic diagnosis, cerebral CT, and cerebral MRI (Magnetic Resonance Imaging) are used.

The ultrasonic diagnosis method can easily non-invasively diagnose atherosclerosis diseases of the carotid artery through carotid ultrasonic diagnosis. Further, an intracranial cerebral hematocele is measured and applied to a clinical study through transcranial Doppler.

The diagnosis method using cerebral CT is good for diagnosis of hemorrhagic diseases, and is a recently developed technique that greatly helps treatment of a patient with a stroke by taking images of a cerebral hematocele state and cerebral vessels.

The diagnosis method using cerebral MRI is not influenced by an artifact due to the skull in comparison to cerebral CT, so it can minutely examine affected parts in the brainstem, the cerebellum, and the temporal lobe, can find out cerebral infarction in the early stage, can finely examine a cerebral perfusion state, and can closely examine a cerebrovascular state, so it can be considered as the best method for examining the state of brain tissues.

In particular, a stroke, which is a disease in which a blood vessel that supplies blood to the brain is clogged or broken, so the brain is damaged and a physical disorder is caused, is the most important factor of death in the world. Further, even if it does not cause death, it is classified as a high-risk disease that causes a permanent disorder.

A stroke was usually considered as a senile disease, but recently, a stroke is frequently shown from thirties and forties, so it is considered as a very dangerous disease that is widely generated even for the youth and manhood.

A stroke may be classified into two types of 'ischemic stroke' that is generated by clogging of a blood vessel that supplies blood to the brain and 'cerebral hemorrhage' in which hemorrhage is generated by a burst of a blood vessel going to the brain.

Ischemic stroke accounts for about 80% of the entire stroke and is generated in most cases when a blood vessel that supplies oxygen and nutriment to the brain is clogged with a thrombus that is a lump of coagulated blood.

Various examinations have been developed to diagnose a stroke and a method of using CT (computed tomography) which is one of the examinations can perform an examination with a relatively short time.

Accordingly, since the method that uses CT has the advantage that a quick examination is possible, it is considered as an examination method that is suitable for the characteristics of a stroke that requires quick measures.

Further, cerebral hemorrhage is observed by CT immediately after hemorrhage is generated, so CT is usefully used as a means that is required to determine cerebral hemorrhage before using a thrombolytic medication, which opens up a clogged blood vessel by dissolving a thrombus, in order to treat ischemic stroke.

In addition, CT is importantly used for observing the progress of cerebral hemorrhage after a thrombolytic medication is used.

In the meantime, an ASPECT (Alberta Stroke Program Early CT) score is used as a representative index that enables determining a stroke.

The ASPECT score divides an MCA (Middle cerebral artery) region into a pre-defined ten anatomic regions and then estimates existence of an early infarct index from non-contrast CT (see the following non-patent document 1).

The ASPECT score has been proved as a strong predictive factor that enables examination of the state of a person with a stroke.

Meanwhile, when the degrees of seriousness of cerebral infarction is given marks through the ASPECT score, etc. on the basis of a cerebral non-contrast CT image, the result of diagnosis becomes different, depending on region determination and analysis by clinical doctors, so there is a problem that it is difficult to maintain consistency in the diagnosis result.

Further, since brain disease analysis apparatuses according to the related art use the method of detecting and then normalizing only encephalopathy from a medical image such as CT or MRI obtained from the diagnosis object, there is a problem that regions extracted from the medical images of patients are not consistent and different, so there is a high possibility of an error when the degrees of seriousness are given marks.

Accordingly, it is required to develop a new technology that can specify cerebral regions, which are vulnerable to cerebral artery damage in a brain image obtained from a diagnosis object, determine the degree of seriousness on the basis of the ratio of encephalopathy in the corresponding cerebral region, and estimate the prognosis of brain damage.

REFERENCES

Patent Document

1. Korean Patent No. 10-1992057 (published on Jun. 24, 2019)
2. Korean Patent No. 10-1754291 (published on Jul. 6, 2017)

Non-Patent Document

1. Barber P A, Demchuk A M, Zhang J, et al. 'Validity and reliability of a quantitative computed tomography score in predicting outcome of hyperacute stroke before thrombolytic therapy: ASPECTS Study Group-Alberta Stroke Programme Early CT Score.' Lancet 2000; 355:1670-74 CrossRef Medline

SUMMARY

Meanwhile, early symptom determination and conversion into an ASPECT score of ischemic stroke are accompanied by considerable interrater variability, which is influenced by a post-experience even of other factors.

That is, the ASPECT score is used as an important factor for estimating a disease by giving the degree of progress of stroke of a user marks from 0 to 10 and enabling medical staffs to determine a treatment method and estimate a prognosis.

However, when a clinical specialist estimates an ASPECT score, the estimated values may vary depending on the careers and experiences of the clinical specialists due to the early symptom of a user and the complexity of images.

Such scoring variability has an advert influence on a decision process for the clinical result of a patient.

Accordingly, it is required to develop a technology that may objectively and automatically estimate an ASPECT score on the basis of an image processing and deep learning technology.

That is, in order to solve the problems described above, an object of the present disclosure is to provide an ASPECT score estimation system and method that estimates an ASPECT score that is a factor for determining a stroke in a non-contrast cerebral CT image.

Another object of the present disclosure is to provide an ASPECT score estimation system and method that may reduce scoring variability when estimating an ASPECT score on the basis of an image processing and deep learning technology.

Another object of the present disclosure is to provide an ASPECT score estimation system and method that may improve reliability of an estimated ASPECT score.

Further, another object of the present disclosure is to provide an image processing apparatus and method using a template that may perform a normalizing process using the template for uniform division of cerebral regions that are vulnerable to cerebral artery damage in medical images of all examinees.

Another object of the present disclosure is to provide a medical image processing apparatus and method using a template that may uniformly divide and extract cerebral regions that are vulnerable to cerebral artery damage from a normalized medical image.

As a result, according to the present disclosure, it is possible to obtain a non-contrast CT image related to the brain of at least one patient, pre-process the non-contrast CT image, determine whether the at least one patient is in a non-hemorrhage state or a hemorrhage state on the basis of the pre-processed image, normalize the pre-processed image, divide and extract an ROI (Region of Interest) using a preset standard mask template, and determine whether there is a possibility of large vessel occlusion in the brain of the at least one patient on the basis of the divided and extracted ROI.

In particular, when there is a possibility of large vessel occlusion in the brain of at least one patient, a determiner estimates an ASPECT score of the at least one patient using a divided and extracted ROI and determines that the at least one patient is a patient to whom mechanical thrombectomy can be applied only when the estimated ASPECT score is a predetermined value or more.

Further, an object of the present disclosure is to provide an apparatus, a system and a method that may increase the clinical test success possibility using a stroke diagnosis method using artificial intelligence for selecting a patient group and a normal group.

The technical subjects to implement in the present disclosure are not limited to the technical problems described above and other technical subjects that are not stated herein will be clearly understood by those skilled in the art from the following specifications.

In order to achieve the objects, a stroke diagnosis apparatus based on AI (Artificial Intelligence) according to an aspect of the present disclosure includes: an image obtainer obtaining a non-contrast CT image related to the brain of at least one patient; a preprocessor pre-processing the non-contrast CT image and determining whether the at least one patient is in a non-hemorrhage state or a hemorrhage state on the basis of the pre-processed image; an image processor normalizing the pre-processed image and dividing and extracting an ROI (Region of Interest) using a preset standard mask template; and a determiner determining whether there is a problem with a cerebral large vessel of the at least one patient using the divided and extracted ROI, in which the determiner estimates an ASPECT score of the at least one patient using the divided and extracted ROI when there is a problem with the cerebral large vessel of the at least one patient, and determines that the at least one patient is a patient to whom mechanical thrombectomy can be applied only when the estimated ASPECT score is a predetermined value or more.

In addition, the preprocessor may include: a noise filter removing noise from the non-contrast CT image; a register performing co-registration spatially aligning images in objects or between a plurality of objects existing in the non-contrast CT image with the noise removed; a skull stripper removing portions that are not a brain structure of the at least one patient from the CT image in which the co-registration has been performed; and a hemorrhage classifier determining whether the at least one patient is in a non-hemorrhage state or a hemorrhage state using the CT image in which skull-stripping has been performed.

When the non-contrast CT image is taken with a gantry inclined, the noise filter may perform a tilt correction function that restores an error due to the inclination through re-sampling using gantry tile header information stored together in the original of the non-contrast CT image.

The register may spatially align images in objects or between a plurality of objects existing in the non-contrast CT image that are derived by at least one of inclination or a difference in brain shape due to movement of the at least one patient when the non-contrast CT image is taken.

The skull stripper may remove portions that are not the brain structure in the CT image on the basis of a skull having a relatively higher Hounsfield unit (HU) value than brain tissues.

The hemorrhage classifier may determine whether the at least one patient is in a non-hemorrhage state or a hemorrhage state using the non-contrast CT image in which skull-stripping has been performed, on the basis of an AI model learning cases related to hemorrhage, and the AI model of the hemorrhage classifier may be learned using voxel information of non-contrast CT data of the at least one patient.

The hemorrhage classifier may make the AI model learn the cases related to hemorrhage using at least one of Intraparenchymal image, Intraventricular image, Subarachnoid image, Subdural image, and Epidural image in the non-contrast CT image in which skull-stripping has been performed.

The hemorrhage classifier may construct the AI model by configuring a convolutional neural network (CNN) to extract feature maps for each data slice of non-contrast CT data of the at least one patient, and applying and combining the extracted plurality of feature maps sequentially with a Long Short-term Memory (LSTM) neural network.

The hemorrhage classifier may determine that the at least one patient is in a hemorrhage state when a specific factor exists in over predetermined regions in the non-contrast CT image in which skull-stripping has been performed regardless of the hemorrhage classification.

The image processor may include: a template setter setting the standard mask template in advance; an image normalizer normalizing the pre-processed image; and an image processor dividing and extracting an ROI by applying the preset standard mask template to the normalized image, in which the image processor may operate only when it is determined that the at least one patient is in the non-hemorrhage state.

The template setter may collect a plurality of medical images obtained from a plurality of normal people and patients with brain diseases, create a 3D normalization image on the basis of the collected images, create a 2D normalization image by slicing the 3D normalization image based on one axis of an X-axis, a Y-axis, and a Z-axis using information of 3D voxels that are predetermined units, and set the standard mask template in advance on the basis of ROIs divided from the created 2D normalization image.

The image normalizer may perform the normalization by changing the Hounsfield unit (HU) value of the pre-processed image.

The determiner may include: an ischemia classifier determining whether there is ischemia in the brain of the at least one patient using the divided and extracted ROI; a large vessel occlusion determiner determining whether there is a problem with a cerebral large vessel of the at least one patient when there is ischemia; an ASPECTS determiner estimating an ASPECT score of the at least one patient using the divided and extracted ROI when there is a problem with the cerebral large vessel; and a thrombectomy determiner determining that the at least one patient is a patient to whom mechanical thrombectomy can be applied only when the estimated ASPECT score is a predetermined value or more.

The ischemia classifier may determine whether there is ischemia on the basis of whether there is an affected part in the divided and extracted ROI and an AI model learning shape classification, and the determination of whether there is an affected part in the divided and extracted ROI and the shape classification may be performed using Old infarct (OI), Recent infarct (RI), Frank hypodensity (FH), and Early ischemic sign (EIS).

The ischemia classifier may determine that there is ischemia when there is at least one of the Old infarct (OI), Recent infarct (RI), Frank hypodensity (FH), and Early ischemic sign (EIS) in any one region of the divided and extracted ROIs.

The problem with the cerebral large vessel may be large vessel occlusion, and the large vessel occlusion determiner may determine whether there is large vessel occlusion on the basis of whether a dense MCA sign has been detected at an infra-ganglionic level in relation to the divided and extracted ROI.

When the dense MCA sign is not detected, the large vessel occlusion determiner may detect a frequency of a Hounsfield unit (HU) value of one of left and right hemispheres of sequential slice images at the infra-ganglionic level in relation to the divided and extracted ROI, and may determine that there is a problem with the cerebral large vessel when the frequency of the detected HU values of at least one of the both hemispheres is a predetermined reference value or more or when a frequency difference of the detected HU values of the both hemispheres is a predetermined difference value or more.

The ASPECTS determiner may estimate the ASPECT score on the basis of whether there is an affected part in the divided and extracted ROI and an AI model learning shape classification, and the determination of whether there is an affected part in the divided and extracted ROI and the shape classification may be performed using Old infarct (OI), Recent infarct (RI), Frank hypodensity (FH), and Early ischemic sign (EIS).

When at least one of the Old infarct (OI), Recent infarct (RI), Frank hypodensity (FH), and Early ischemic sign (EIS) is detected, the ASPECTS determiner may admit it as an affected part and reflect the value admitted as an affected part to estimation of the ASPECT score.

When the Frank hypodensity (FH) and Early ischemic sign (EIS) of the Old infarct (OI), Recent infarct (RI), Frank hypodensity (FH), and Early ischemic sign (EIS) are detected, the ASPECTS determiner may admit them as an affected part and reflect the value admitted as an affected part to the estimation of the ASPECT score.

The divided and extracted ROI may include an MCA (Middle cerebral artery), ACA (Anterior cerebral artery), PCA (Posterior cerebral artery), and ICA (Internal carotid artery) regions, and when the Frank hypodensity (FH) and the Early ischemic sign (EIS) of the Old infarct (OI), Recent infarct (RI), Frank hypodensity (FH), and Early ischemic sign (EIS) are detected in the MCA, ACA, PCA, and ICA regions, the ASPECTS determiner may admit them as affected parts and reflect the values admitted as affected parts to the estimation of the ASPECT score.

When the estimated ASPECT score is a predetermined value or more, the thrombectomy determiner may determine that the at least one patient is a patient to whom mechanical thrombectomy can be applied, only when a reference determined through the information obtained by the ischemia classifier and the information obtained by the large vessel occlusion determiner is a predetermined reference or more.

The thrombectomy determiner may determine whether the at least one patient is a patient to whom mechanical thrombectomy can be applied, on the basis of an AI model detecting and learning the size, the volume, or the density of an affected part generated due to a problem with the cerebral large vessel.

The thrombectomy determiner may calculate a tissue clock using an absolute time, and the volume or density of Early ischemic sign (EIS) or Frank hypodensity (FH) until non-contrast CT imaging after a problem with the cerebral large vessel is generated, and determine whether the at least one patient is a patient to whom mechanical thrombectomy can be applied, on the basis of the calculated tissue clock.

The stroke diagnosis apparatus may further include a communication unit transmitting information about the at least one patient to a pre-designated outside when the at least one patient is a patient to whom mechanical thrombectomy can be applied.

The information that is transmitted to the outside may include elapsed time information, original non-contrast CT information, determination result information, tissue clock information, and the estimated ASPECT score information that are related to the at least one patient.

According to the ASPECT score estimation system and method of the present disclosure, there is an effect that it is possible to estimate an ASPECT score that is an objective index for examining the state of a patient with a stroke using the cerebral CT image of the patient.

Further, according to the present disclosure, there is an effect that it is possible to prevent problems due to scoring variability among specialists and it is possible to be used as a reliable index that can make determination of treatment for a patient at a medical site easy, due to the features of a stroke disease that requires quick prescription.

Further, according to the present disclosure, there is an effect that it is possible to overcome inaccuracy of a score value caused by the complexity of the method of estimating an ASPECT score for a stroke through cerebral CT image analysis and the careers of specialists due to the requirement of professionalism.

Further, according to the present disclosure, there is an effect that it is possible to remarkably reduce the manpower and the time and economic costs for an analysis process by automating the entire process of CT image-based stroke analysis.

Further, according to the present disclosure, there is an effect that it is possible to consistently divide and extract a brain region that is vulnerable to cerebral artery damage by normalizing a medical image of a brain such as CT or MRI and applying a preset standard mask template to the normalized medical image.

Further, according to the present disclosure, there is an effect that it is possible to consistently divide and extract an ROI from medical images of all examinees on the basis of a normalized image after normalizing the medical images of diagnosis targets through a template.

As described above, since a brain disease (stroke) is analyzed and diagnosed through an ROI divided and extracted on the basis of a standard mask template, there is an effect that it is possible to maximize precision and accuracy of a diagnosis result.

As a result, according to the present invention, there is provided an effect that it is possible to obtain a non-contrast CT image related to the brain of at least one patient, pre-process the non-contrast CT image, determine whether the at least one patient is in a non-hemorrhage state or a hemorrhage state on the basis of the pre-processed image, normalize the pre-processed image, divide and extract a region of interest (ROI) using a preset standard mask template, and determine whether there is a possibility of large vessel occlusion in the brain of the at least one patient on the basis of the divided and extracted ROI.

In particular, according to the present disclosure, when there is a possibility of large vessel occlusion in the brain of at least one patient, a determiner may estimate an ASPECT score of the at least one patient using a divided and extracted ROI and may determine that the at least one patient is a patient to whom mechanical thrombectomy can be applied only when the estimated ASPECT score is a predetermined value or more.

Further, the result of a clinical examination for proving the efficacy of a remedy is determined by confirming statistical significance about whether an expected effect estimated in advance is achieved for the participants in the clinical examination, and when the stroke diagnosis method and apparatus according to the present disclosure is applied, only patients with a stroke that is accurately aimed by a new medicine are included in clinical examination objects, thereby being able to maximally increase the clinical examination success possibility.

That is, it is possible to use the stroke diagnosis method using AI according to the present disclosure in order to increase a clinical test success possibility by using the method to select a patient group and a normal group.

Meanwhile, the effects of the present disclosure are not limited to the effects described above and other effects can be clearly understood by those skilled in the art from the following description.

BRIEF DESCRIPTION OF THE DRAWINGS

The above and other aspects, features and other advantages of the present disclosure will be more clearly understood from the following detailed description taken in conjunction with the accompanying drawings, in which:

FIG. 16 is a view showing a method of increasing a clinical test success possibility using a stroke diagnosis method using AI for selecting a patient group and a normal group.

DETAILED DESCRIPTION OF THE PREFERRED EMBODIMENT

Hereinafter, an exemplary embodiment of the present disclosure will be described in detail with reference to the accompanying drawings. Further, the embodiment to be described below does not unfairly limit the contents of the present disclosure described in claims and the entire configuration described in the embodiment should not be construed as being necessary as a means for solution of the present disclosure.

Hereafter, a stroke diagnosis apparatus and method based on AI (Artificial Intelligence) according to an exemplary embodiment of the present disclosure is described in detail with reference to the accompanying drawings.

Stroke Diagnosis Apparatus Based on AI (Artificial Intelligence)

Figure 1:
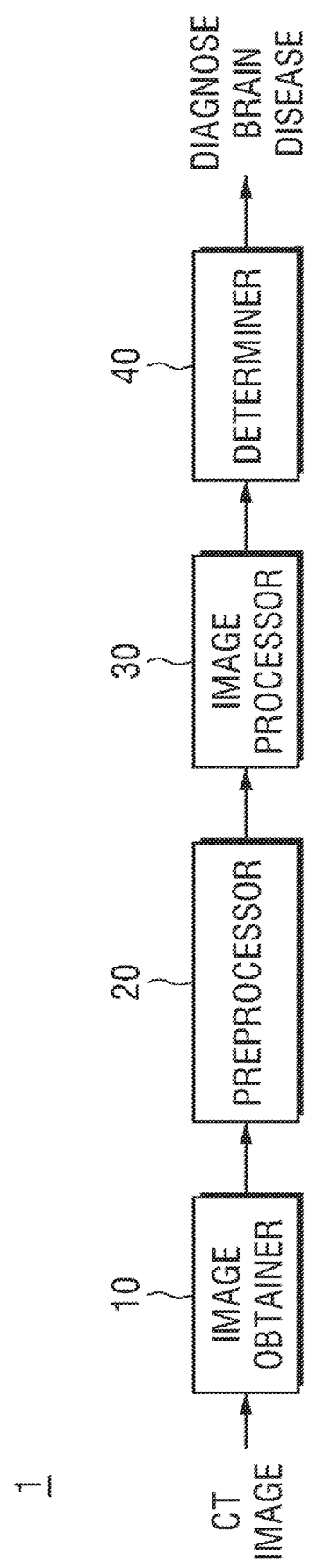
FIG. 1 is an exemplary block configuration diagram of a stroke diagnosis apparatus based on AI (Artificial Intelligence) of the present disclosure.

FIG. 1 is an exemplary block configuration diagram of a stroke diagnosis apparatus based on AI of the present disclosure.

A stroke diagnosis apparatus 1 based on AI according to the present disclosure may include an image obtainer 10, a preprocessor 20, an image processor 30, and a determiner 40.

First, the image obtainer 10 is a device that obtains a medical image by taking a picture of a brain of the object to be diagnosed.

The image obtainer 10 may obtain images from photographing equipment that is taking various medical images such as cerebral CT, MRI, etc.

Representatively, the image obtainer 10 of the present disclosure may obtain cerebral CT images.

Next, the preprocessor 20 provides a function that discriminates non-hemorrhage and hemorrhage in accordance with an AI algorithm on the basis of a non-contrast CT image.

Further, the image processor 30 provides a function that normalizes a medical image obtained from the preprocessor 20 and divides and extracts an ROI (Region of Interest) using a preset standard mask template.

Further, the determiner 40 may diagnose a brain disease due to cerebral artery damage by analyzing the divided and extracted ROI.

The determiner 40 according to the present disclosure enables medical staffs to easily and directly give marks to the degrees of seriousness of a brain disease due to cerebral artery damage on the basis of a medical image of the divided and extracted ROI, thereby being able to help the medical staffs diagnose a brain disease and estimate a prognosis.

Hereafter, the detailed technological features of the preprocessor 20, the image processor 30, and the determiner 40 that are components of the stroke diagnosis apparatus 1 are described with reference to the drawings.

Preprocessor

The preprocessor 20 according to the present disclosure provides a function that discriminates non-hemorrhage and hemorrhage in accordance with an AI algorithm on the basis of a non-contrast CT image.

Figure 2:
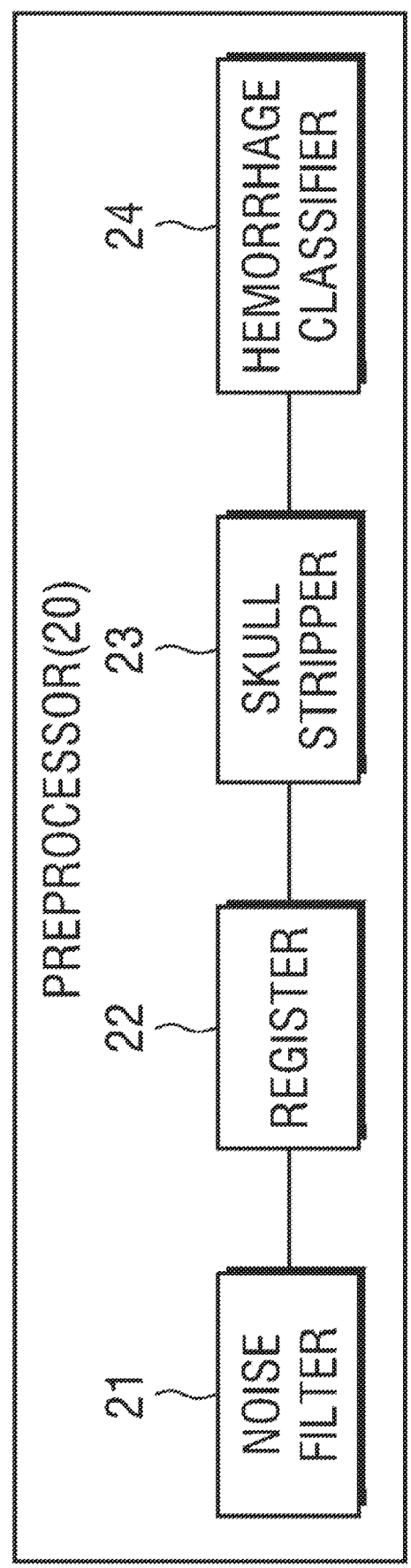
FIG. 2 is an exemplary block configuration diagram of a preprocessor described with reference to FIG. 1.

FIG. 2 is an exemplary block configuration diagram of the preprocessor described with reference to FIG. 1.

Referring to FIG. 2, the preprocessor 20 according to the present disclosure may include a noise filter 21, a register 22, a skull stripper 23, and a hemorrhage classifier 24.

First, the noise filter 21 performs an operation of removing noise from images collected from the image obtainer 10.

Representatively, the noise filter 21 performs a tilt correction function related to a gantry that is a component of a CT imaging apparatus.

In some head CT scanning, an inclined image slice is frequently obtained due to inclination of a gantry, and when photographing is performed with a gantry inclined, the distances of voxels between image slices are not correct and particularly there may be a problem with 3D visualization.

Accordingly, the noise filter 21 according to the present disclosure may restore an error due to inclination through re-sampling using 'Gantry/Detector Tilt header' information of the information stored together with a DICOM original image when photographing is performed with a gantry inclined.

By performing gantry tilt correction in an early stage in this way, it is possible to expect improvement of the performance of analysis.

Next, the register 22 provides a co-registration function.

The co-registration function of the present disclosure is to align images to align anatomical structures, which means spatially aligning images in objects or between objects according to inclination due to movement of examinees or the difference in brain shape of examinees during CT imaging.

Further, the skull stripper 23 provides a skull-stripping function that provides a function for removing parts that are not the brain structure from a CT image.

Since the skull has a relatively higher HU (Hounsfield unit) value than the brain tissues in a CT image, in the present disclosure, analysis is performed after parts that are not the brain structure through the skull stripper 23, thereby increasing easiness of analysis of the affected part of brain tissues.

Further, the hemorrhage classifier 24 provides a function that learns and classifies hemorrhage types on the basis of AI.

For learning a hemorrhage type of the hemorrhage classifier 24, voxel information of non-contrast CT data of a patient may be used.

That is, the hemorrhage classifier 24 may construct and use an AI model architecture that configures a CNN (Convolutional neural network) for feature extraction for individual NCCT slice and combines an LSTM (Long Short-term Memory) neural network for considering all serial slices of a patient.

On the basis of this, the hemorrhage classifier 24 calculates output for whether each patient has hemorrhage and hemorrhage type classification of positive patients.

As another method, it may be possible to use a method that classifies a patient as a patient with hemorrhage on the basis of hemorrhage when the hemorrhage is shown in over a predetermined region in an image, regardless of the hemorrhage types.

As another method, the hemorrhage classifier 24 according to the present disclosure may use Intraparenchymal, Intraventricular, Subarachnoid, Subdural, Epidural, etc., to detect and classify a hemorrhage-estimated affected part in a CT image.

Further, in the present disclosure, it may be possible to independently perform pre-processing and data input in the step of classifying hemorrhage and ischemia by transmitting an ID information list of negative hemorrhage patients to an ischemia classification AI model of the determiner 40.

Thereafter, a non-hemorrhage state and a hemorrhage state may be discriminated in accordance with the AI algorithm of the hemorrhage classifier 24.

Image Processor

The image processor 30 according to the present disclosure means a medical image processing device that provides a function that normalizes a medical image obtained from the preprocessor 20 and divides and extracts an ROI (Region of Interest) using a preset standard mask template.

Figure 3:
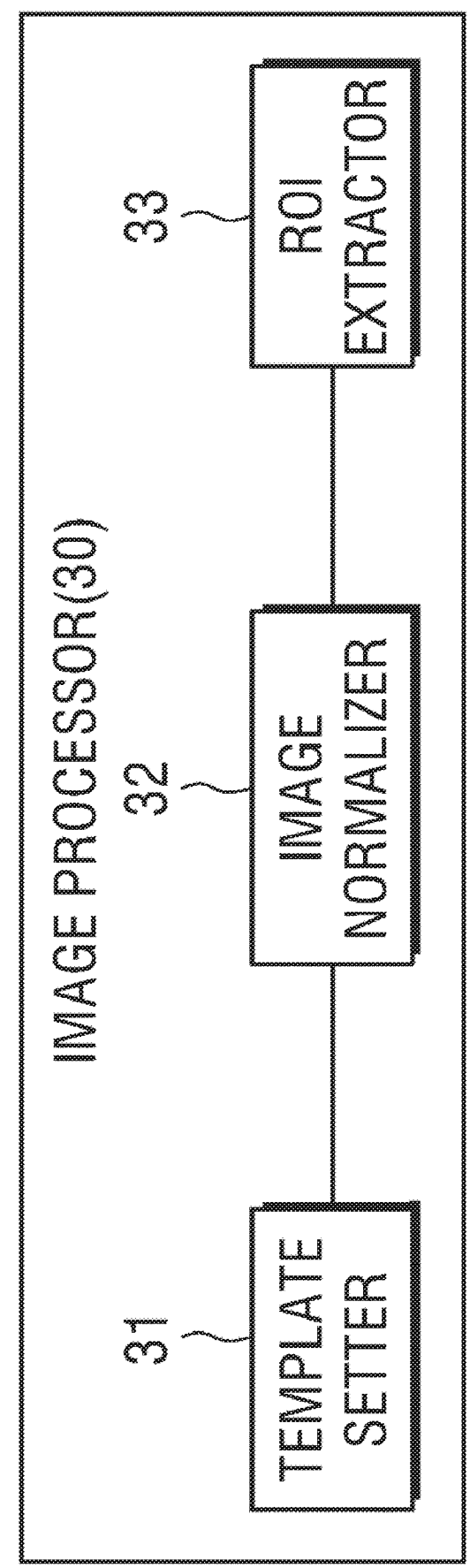
FIG. 3 is an exemplary block configuration diagram of an image processor described with reference to FIG. 1.

FIG. 3 is an exemplary block configuration diagram of the image processor described with reference to FIG. 1.

Referring to FIG. 3, the image processor 30 according to the present disclosure may include a template setter 31, an image normalizer 32, and an ROI extractor 33.

First, the template setter 31 sets a standard mask template for dividing and extracting an ROI from a medical image.

The template setter 31 collects a plurality of medical images obtained from a plurality of normal people and patients with brain diseases from the preprocessor 20, creates 2D and 3D normalization images, and creates a 2D normalization image by performing sliding along a specific axis in accordance with voxel setting on the basis of the 3D normalization image.

The present disclosure, before dividing and extracting an ROI from a medical image of a diagnosis object, extracts an ROI from a plurality of medical images obtained from a plurality of normal people and patients with brain diseases, and creates a standard mask template of the ROI for diagnosing a brain disease of the diagnosis object.

The template setter 31 may create a 2D normalization image by setting voxels in a predetermined unit, for example, in mm about the X-axis, Y-axis, and Z-axis of a 3D normalization image.

Further, the template setter 31 divides an ROI in the created 2D normalization image and creates a standard mask template on the basis of ROIs divided from a plurality of normalization images.

Next, the image normalizer 32 provides a function that normalizes a medical image of a diagnosis object.

For example, the image normalizer 32 may normalize an image through a process of correcting a non-uniform bias in an original medical image of a diagnosis object, performing co-registration through spatial alignment, and performing spatial normalization by applying a standard stereotaxic space.

Obviously, the present disclosure is not necessarily limited thereto and may normalize a medical image in various ways.

Further, the ROI extractor 33 provides a function that divides and extracts an ROI by applying a standard mask template to a normalized medical image.

The ROI extractor 33 divides and extracts an ROI by discriminating territories related to Anterior/Middle/Posterior cerebral arteries (ACA, MCA, PCA) and dividing a brain structure related to ACA, MCA, PCA territories in each of the left and right hemispheres.

A medical image including an ROI divided and extracted in this way is transmitted to the determiner 40.

Determiner

The determiner 40 may diagnose a brain disease due to cerebral artery damage by analyzing the divided and extracted ROI. That is, the determiner 40 according to the present disclosure enables medical staffs to easily and directly give marks to the degrees of seriousness of a brain disease due to cerebral artery damage on the basis of a medical image of the divided and extracted ROI, thereby being able to help the medical staffs diagnose a brain disease and estimate a prognosis.

Figure 4:
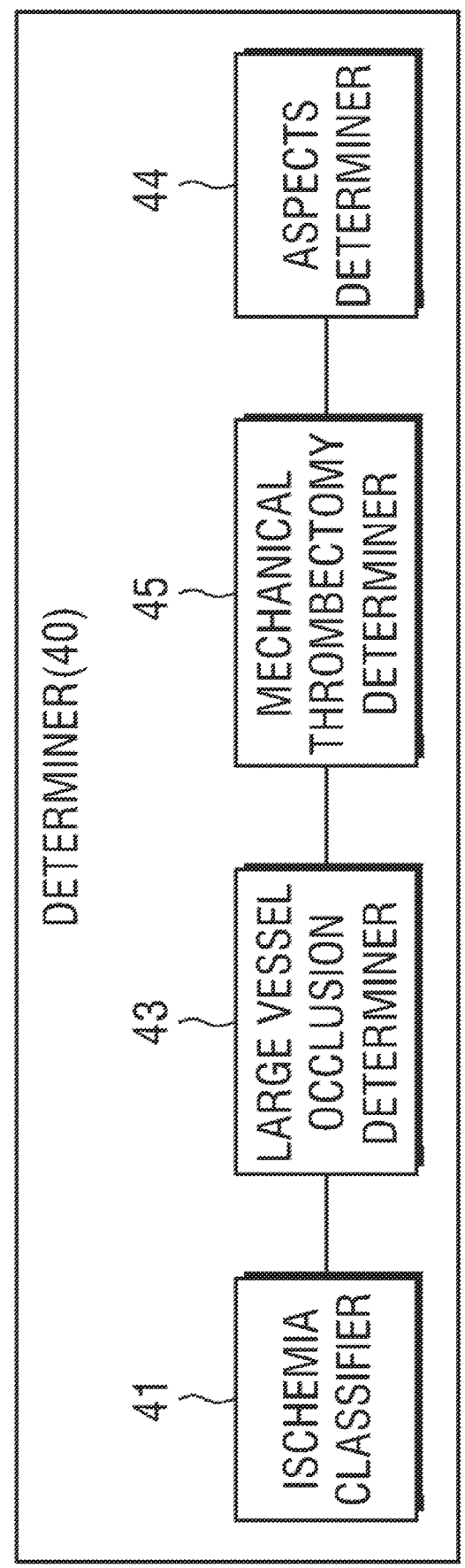
FIG. 4 is an exemplary block configuration diagram of a determiner described with reference to FIG. 1.

FIG. 4 is an exemplary block configuration diagram of the determiner described with reference to FIG. 1.

Referring to FIG. 4, the determiner 40 according to the present disclosure may include an ischemia classifier 41, a large vessel occlusion determiner 43, an ASPECTS determiner 44, and a mechanical thrombectomy determiner 45.

First, the ischemia classifier 41 determines whether a non-hemorrhage patient has ischemia by receiving an ROI divided and extracted by applying a standard mask template to a normalized medical image by the ROI extractor 33.

The ischemia classifier 41 according to the present disclosure may use a method of determining whether there is an affected part in a divided region and classifying the shape, using AI.

That is, the ischemia classifier 41 according to the present disclosure may independently perform determining whether there is an affected part in each divided region and classifying the shape in relation to Old infarct (OI)/Recent infarct (RI)/Frank hypodensity (FH)/Early ischemic sign (EIS).

Thereafter, the ischemia classifier 41 determines only FH/EIS as an acutely affected part in the left and right divided hemispheres of the brain, and when there is an acutely affected part, it determines that a non-hemorrhage patient has ischemia.

When a non-hemorrhage patient has ischemia, the large vessel occlusion determiner 43 determines whether the patient has large vessel occlusion.

Whether there is a possibility of large vessel occlusion may be determined on the basis of whether a dense MCA sign has been detected at an infra-ganglionic level.

Meanwhile, even though large vessel occlusion is generated, a case in which a dense MCA sign is not detected may intermittently occur.

Accordingly, in the present disclosure, even if a dense MCA sign is not detected, the large vessel occlusion determiner 43 derives the frequency difference of Hounsfield unit (HU) values of the left and right hemispheres in sequential slice images at the infra-ganglionic level, thereby being able to make up for the problem.

That is, the large vessel occlusion determiner 43 according to the present disclosure may determine that there is large vessel occlusion when the frequency of the detected HU value of at least one of both hemispheres is a predetermined reference value or more or when the frequency difference of the detected HU values of both hemispheres is a predetermined difference value or more.

If a patient does not have large vessel occlusion, a conservative treatment process is performed, but when a patient has large vessel occlusion, it is required to determine whether mechanical thrombectomy can be applied to the patient.

Whether mechanical thrombectomy can be applied to a patient may be determined by the ASPECTS determiner 44 and the mechanical thrombectomy determiner 45.

First, the ASPECTS determiner 44 receives an ROI divided and extracted by applying a standard mask template to a normalized medical image by the ROI extractor 33, and calculates an ASPECT score.

The ASPECTS determiner 44 may calculate an ASPECT score through detection of an affected part and shape classification.

Old infarct (OI)/Recent infarct (RI)/Frank hypodensity (FH)/Early ischemic sign (EIS), etc. may be representative of detection of an affected part and shape classification.

In this case, a conventional ASPECTS calculation method that admits an affected part as long as at least one of OI/RI/FH/EIS is detected by applying an AI algorithm may be applied.

In this case, it is possible to reduce the score by reflecting the value admitted as an affected part to estimation of the ASPECT score.

Further, in the present disclosure, a modified ASPECTs method that admits only detection of FH/EIS as an affected part by applying an AI algorithm may be applied.

In this case, it is possible to reduce the score by reflecting the value admitted as an affected part to estimation of the ASPECT score.

Further, in the present disclosure, an extended ASPECTS calculation method that adds a region related to ACA, PCA, and ICA and admits only detection of FH/EIS as an affected part by applying an AI algorithm may be applied.

In general, the region where ASPECTS is calculated is an MCA (Middle cerebral artery) territory. In the present invention, the region is extended to ACA (Anterior cerebral artery), PCA (Posterior cerebral artery), and ICA (Internal carotid artery) regions, when Frank hypodensity (FH) and Early ischemic sign (EIS) of the Old infarct (OI), Recent infarct (RI), Frank hypodensity (FH), and Early ischemic sign (EIS) are detected in the MCA, ACA, PCA, and ICA regions, the ASPECTS determiner 44 may admit them as affected part and may reflect the values admitted as affected parts to estimation of the ASPECT score.

Further, the mechanical thrombectomy determiner 45 determines whether mechanical thrombectomy can be applied to the patient, using the ASPECT score transmitted from the ASPECTS determiner 44.

When there is a possibility of the patient having large vessel occlusion and the score is lower than a specific reference, there is little possibility of recovery, so the mechanical thrombectomy determiner 45 determines that mechanical thrombectomy cannot be applied, using the ASPECT score transmitted from the ASPECTS determiner 44, and progresses a conservative treatment.

However, even if the patient has large vessel occlusion, when the ASPECT score transmitted from the ASPECTS determiner 44 is a predetermined value or more, there is a possibility of recovery, so it is determined that mechanical thrombectomy can be applied to the patient.

When it is determined that mechanical thrombectomy can be applied to the patient, various items of information about the patient may be transmitted to a tertiary hospital.

Transmission of information to a tertiary hospital is not shown in the drawings, but it may be performed by a communication unit and the communication unit may transmit corresponding information to a pre-designated outside (e.g., a hospital, etc.) through short range communication or long distance communication.

The long distance communication that can be used in this case may be WLAN (Wireless LAN) (Wi-Fi), Wibro (Wireless broadband), Wimax (World Interoperability for Microwave Access), HSDPA (High Speed Downlink Packet Access), etc.

Further, the technology of short range communication may be Bluetooth, RFID (Radio Frequency Identification), IrDA (infrared Data Association), UWB (Ultra-Wideband), ZigBee, etc.

Stroke Diagnosis and Classification Method Based on AI

Figure 5:
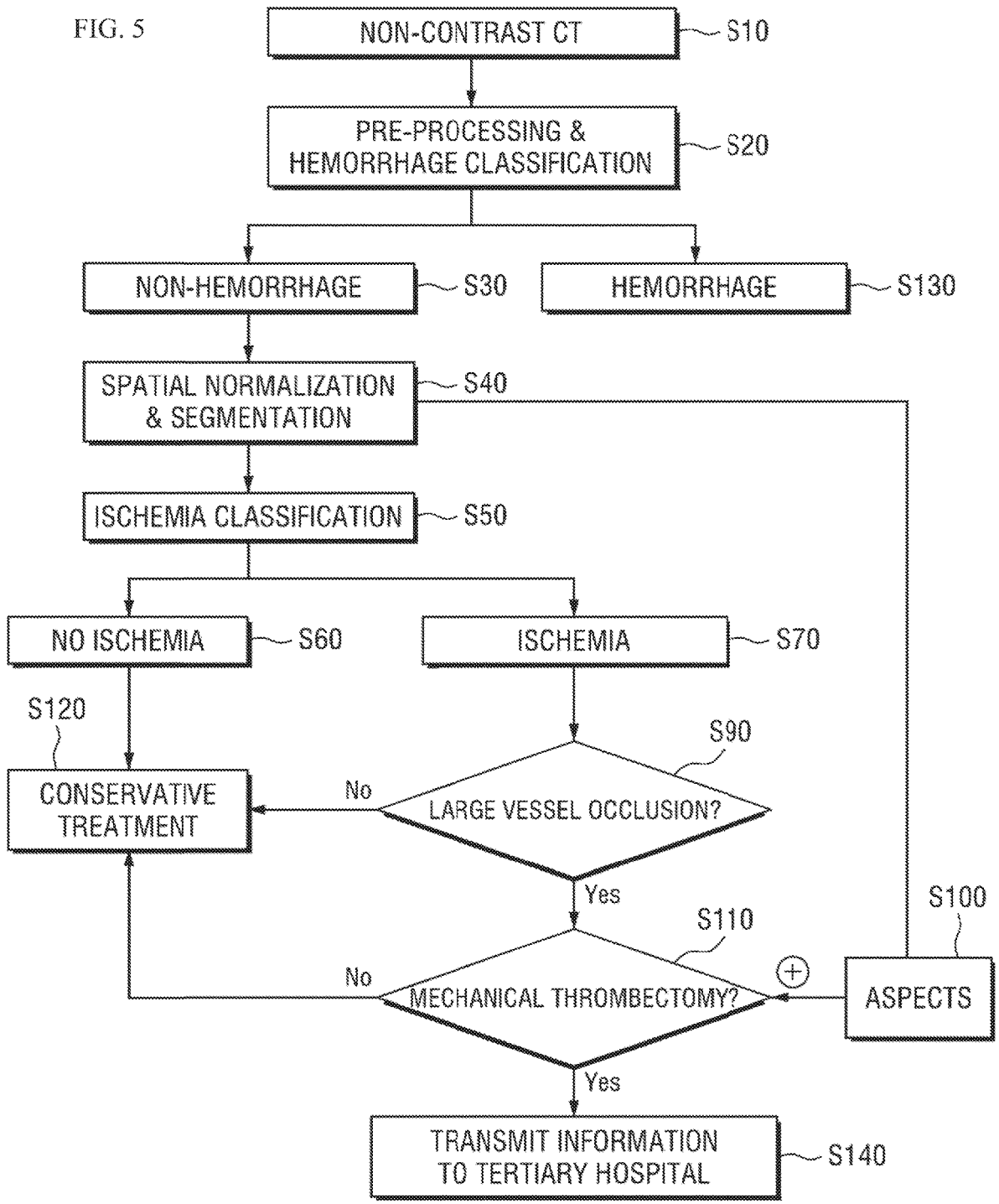
FIG. 5 is an exemplary flowchart showing the entire process of a stroke diagnosis method based on AI proposed by the present disclosure.

FIG. 5 is an exemplary flowchart showing the entire process of a stroke diagnosis method based on artificial intelligence of the present disclosure.

Referring to FIG. 5, first of all, a step (S10) in which the image obtainer 10 obtains a non-contrast CT image is performed.

Thereafter, the preprocessor 20 performs pre-processing and hemorrhage classification (S20).

The pre-processing and hemorrhage classification step (S21) may include a step (S21) in which the noise filter removes noise, a step (S22) in which co-registration function is performed, a step (S23) in which the skull stripper 23 performs a skull-stripping function, and a step (S24) in which the hemorrhage classifier 24 learns a hemorrhage type on the basis of AI and discriminates a non-hemorrhage state (S30) and a hemorrhage state (S130) in accordance with an AI algorithm on the basis of a learning model.

The details of the step (S20) will be described below with reference to FIG. 6.

After the step (S20), a non-hemorrhage state (S30) and a hemorrhage state (S130) are discriminated in accordance with an AI algorithm on the basis of a learning model, and when it is the non-hemorrhage state (S30), a spatial normalization and segmentation step (S40) is progressed.

The spatial normalization and segmentation step (S40) may be performed through a step of creating a 3D normalization image (S41), a step of setting voxel and creating a 2D normalization image (S42), a step of dividing an ROI and creating a mask template (S43), a step of collecting and normalizing a plurality of medical images (S44), and a step of applying a mask template and dividing and extracting an ROI (S45).

The details of the step (S40) will be described below with reference to FIG. 7.

After the spatial normalization and segmentation step (S40), a process (S50) of classifying ischemia on the basis of the divided and extracted ROI by applying a standard mask template to the normalized medical image is progressed.

In the step (S50), the ischemia classifier 41 determines whether a non-hemorrhage patient has ischemia by receiving an ROI divided and extracted by applying a standard mask template to a normalized medical image by the ROI extractor 33.

The details of the step (S50) will be described below with reference to FIG. 10.

If a non-hemorrhage patient does not have ischemia in the step (S50), a conservative treatment step (S120) is progressed.

However, when it is determined that a non-hemorrhage patient has ischemia (S70), the large vessel occlusion determiner 43 determines whether the patient has large vessel occlusion (S90).

Whether the large vessel occlusion has been generated in the step (S90) may be determined on the basis of whether a dense MCA sign has been detected at an infra-ganglionic level.

Meanwhile, even though the large vessel occlusion is generated, a case in which a dense MCA sign is not detected may be intermittently generated.

Accordingly, in the present disclosure, even if a dense MCA sign is not detected, the large vessel occlusion determiner 43 derives the frequency difference in Hounsfield unit (HU) value of the left and right hemispheres in sequential slice images at the infra-ganglionic level, thereby being able to make up for the problem.

That is, the large vessel occlusion determiner 43 according to the present disclosure may determine that there is large vessel occlusion when the frequency of the detected HU value of at least one of both hemispheres is a predetermined reference value or more or when the frequency difference of the detected HU values of both hemispheres is a predetermined difference value or more.

The details of the step (S90) will be described below with reference to FIG. 11.

If a patient does not have large vessel occlusion, a conservative treatment process (S120) is performed, but when a patient has large vessel occlusion, it is required to determine whether mechanical thrombectomy can be applied to the patient.

Accordingly, in order to determine whether mechanical thrombectomy can be applied to the patient, a step of estimating an ASPECT score (S100) is performed after the step (S90).

In relation to the step (S100), the ASPECTS determiner 44 receives an ROI divided and extracted by applying a standard mask template to a normalized medical image by the ROI extractor 33, and calculates an ASPECT score.

The details of the step (S100) will be described below with reference to FIG. 12.

After the step (S100), the mechanical thrombectomy determiner 45 determines whether mechanical thrombectomy can be applied to the patient, using the ASPECT score transmitted from the ASPECTS determiner 44 (S110).

When the patient has large vessel occlusion and the score is lower than a specific reference, there is little possibility of recovery, so the mechanical thrombectomy determiner 45 determines that mechanical thrombectomy cannot be applied, using the ASPECT score transmitted from the ASPECTS determiner 44, and progresses a conservative treatment (S120).

However, even if the patient has large vessel occlusion, when the ASPECT score transmitted from the ASPECTS determiner 44 is a specific reference or more, there is a possibility of recovery, so it is determined that mechanical thrombectomy can be applied to the patient. When it is determined that mechanical thrombectomy can be applied to the patient, various items of information about the patient can be transmitted to a tertiary hospital (S140).

The information that is transmitted to a tertiary hospital may be at least one of an elapsed time, a non-contrast CT image, a determination result and tissue clock information, conventional ASPECTS information, modified ASPECTS information, and extended ASPECTS information.

Hereafter, the respective steps of the entire process of the stroke diagnosis method based on AI described with reference to FIG. 5 are described in detail with reference to the drawings.

Pre-Processing and Hemorrhage Classification Process

Figure 6:
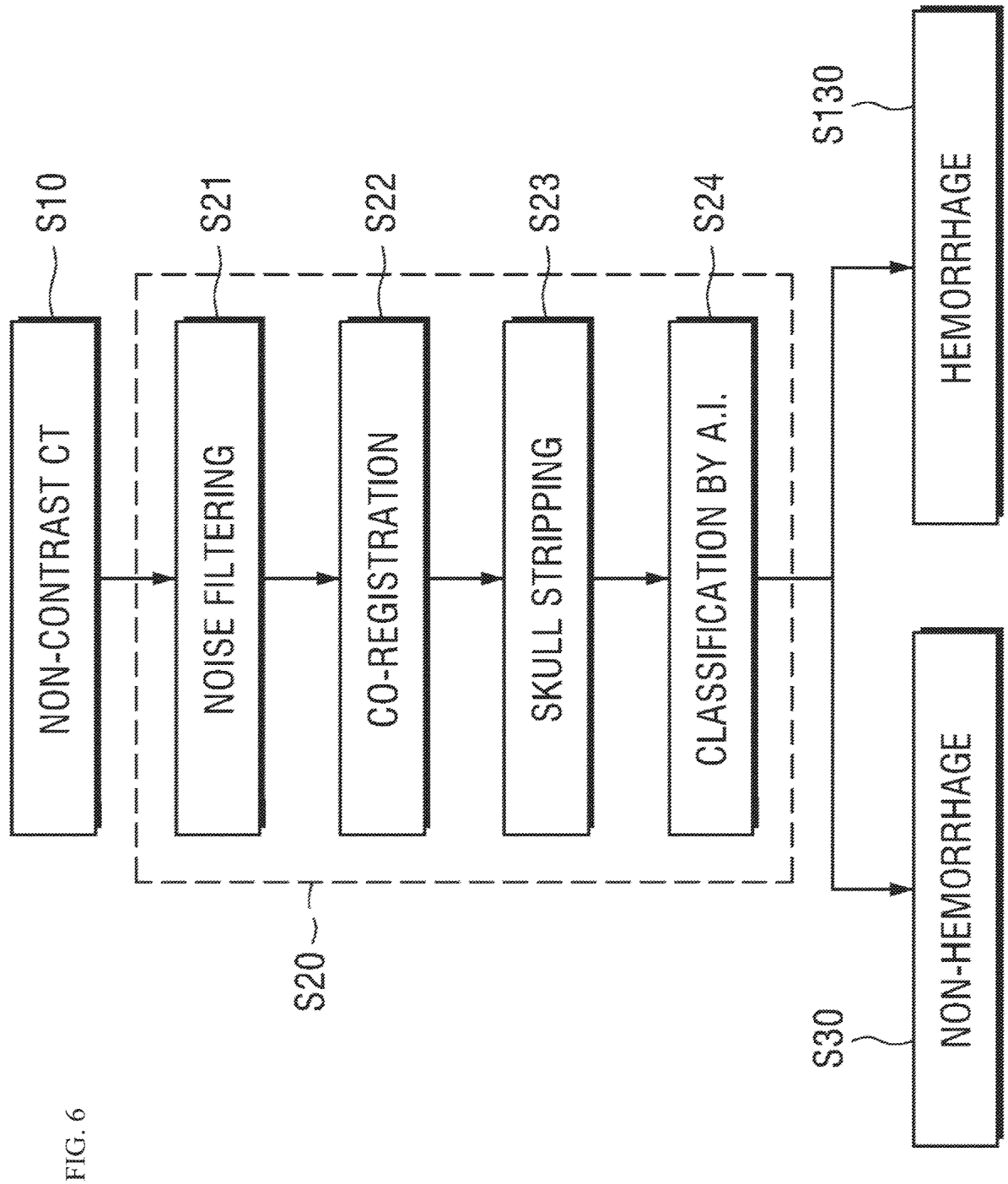
FIG. 6 is a flowchart showing a process of pre-processing and hemorrhage classification based on a non-contrast CT image in the process described with reference to FIG. 5.

FIG. 6 is a flowchart showing a process of pre-processing and hemorrhage classification based on a non-contrast CT image in the process described with reference to FIG. 5.

Referring to FIG. 6, first, a non-contrast CT image is obtained (S10), and on the basis of the non-contrast CT image, the noise filter 21 of the preprocessor 20 removes noise from images collected from the image obtainer 10 (S21).

In the step (S21), the noise filter 21 may perform a tilt correction function related to a gantry that is a component of a CT apparatus.

In head CT scanning, an inclined image slice is frequently obtained due to inclination of a gantry, and when photographing is performed with a gantry inclined, the distances of voxels between image slices are not correct and particularly there may be a problem with 3D visualization. Accordingly, in the step (S21), it is possible to restore an error due to inclination through re-sampling using 'Gantry/Detector Tilt header' information of the information stored together with a DICOM original image when photographing is performed with a gantry inclined.

Since noise included in a CT image is a factor that decreases the accuracy in the steps included in the pre-processing step for obtaining main features of the brain, it should be removed, and in the step (S21), it is possible to remove noise included in an image by convoluting Gaussian blur in the entire image.

By performing gantry tilt correction in the step (S21) in this way, it is possible to expect improvement of the performance of analysis.

Next, the register 22 performs a co-registration function (S22).

In the step (S22), the register 22 aligns images to arrange anatomical structures, which means spatially aligning images in objects or between objects according to inclination due to movement of examinees or the difference in brain shape of examinees during CT imaging.

After the step (S22), the skull stripper 23 performs a skull-stripping function that provides a function for removing parts that are not the brain structure from a CT image (S23).

That is, since the skull has a relatively higher HU (Hounsfield unit) value than the brain tissues in a CT image, analysis is performed after parts that are not the brain structure through the step (S23), thereby increasing easiness of analysis of the affected part of brain tissues.

After the step (S23), the hemorrhage classifier 24 may learn the hemorrhage type on the basis of AI and may discriminate a non-hemorrhage state (S30) and a hemorrhage state (S130) in accordance with an AI algorithm on the basis of a learning model (S24).

In the step (S24), when learning the hemorrhage type, the hemorrhage classifier 24 may construct and use an AI model architecture that configures a CNN (Convolutional neural network) for feature extraction for individual non-contrast CT slice images and combines an LSTM (Long Short-term Memory) neural network for considering all serial slices of a patient. Further, on the basis of this, the hemorrhage classifier 24 calculates output for whether each patient has hemorrhage and hemorrhage type classification of positive patients.

As another method, it may be possible to use a method that classifies a patient as a patient with hemorrhage on the basis of hemorrhage when the hemorrhage is shown in over a predetermined region in an image, regardless of the hemorrhage types.

As another method, the hemorrhage classifier 24 according to the present disclosure may use Intraparenchymal, Intraventricular, Subarachnoid, Subdural, Epidural, etc., to detect and classify a hemorrhage-estimated affected part in a CT image.

Spatial Normalization and Segmentation Process

Figure 7:
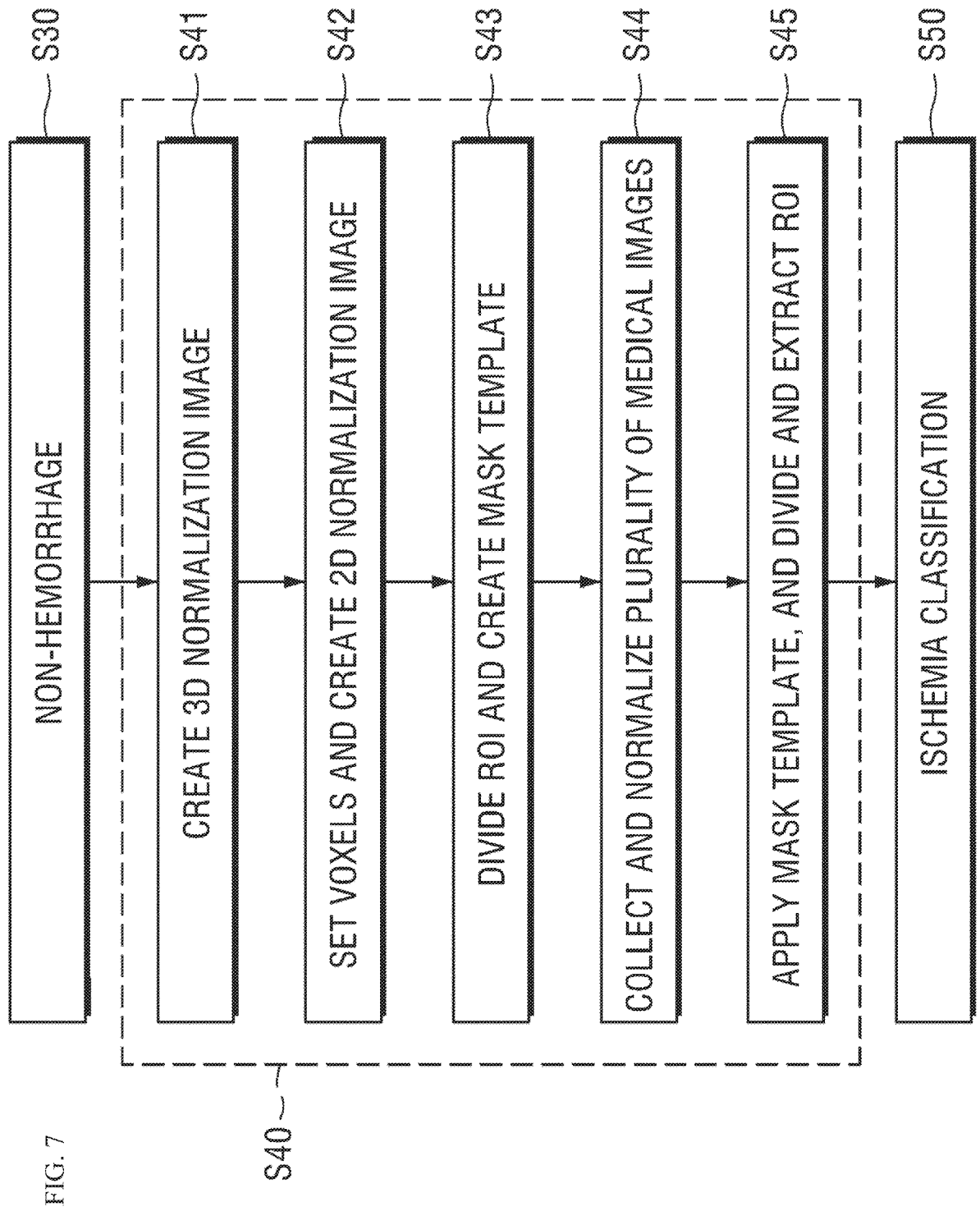
FIG. 7 is a flowchart showing a spatial normalization and segmentation process in the process described with reference to FIG. 5.

FIG. 7 is a flowchart showing a spatial normalization and segmentation process in the process described with reference to FIG. 5.

Referring to FIG. 7, after a non-hemorrhage is determined (S30), the spatial normalization and segmentation step (S40) is progressed.

The spatial normalization and segmentation step (S40) is described in detail on the basis of FIG. 7.

First of all, the template setter 31 collects a plurality of medical images obtained from a plurality of normal people and patients with brain diseases from the preprocessor 20, and creates a 3D normalization image (S41).

Thereafter, the template setter 31 creates a 2D normalization image by setting voxels on the basis of the 3D normalization image (S42).

In the step (S42), the template setter 31 may create a 2D normalization image by setting a voxel in a predetermined unit, for example, in mm about the X-axis, Y-axis, and Z-axis of a 3D normalization image.

That is, it is possible to create a 2D normalization image by slicing the 3D normalization image about one of the X-axis, Y-axis, and Z-axis in accordance with 3D voxel setting that is a predetermined unit.

The normalization image is 3D and the voxels are also 3D, but when a normalization image is displayed using voxels by setting one axis of the X-axis, Y-axis, and Z-axis as a reference axis, a normalization image converted into 2D may be created.

After the step (S42), the template setter 31 divides an ROI in the created 2D normalization image and creates a standard mask template on the basis of ROIs divided from a plurality of normalization images (S43).

FIGS. 8A-8E are views exemplifying a process of dividing a normalized image by creating a standard mask template in FIG. 7.

Figure 8A:
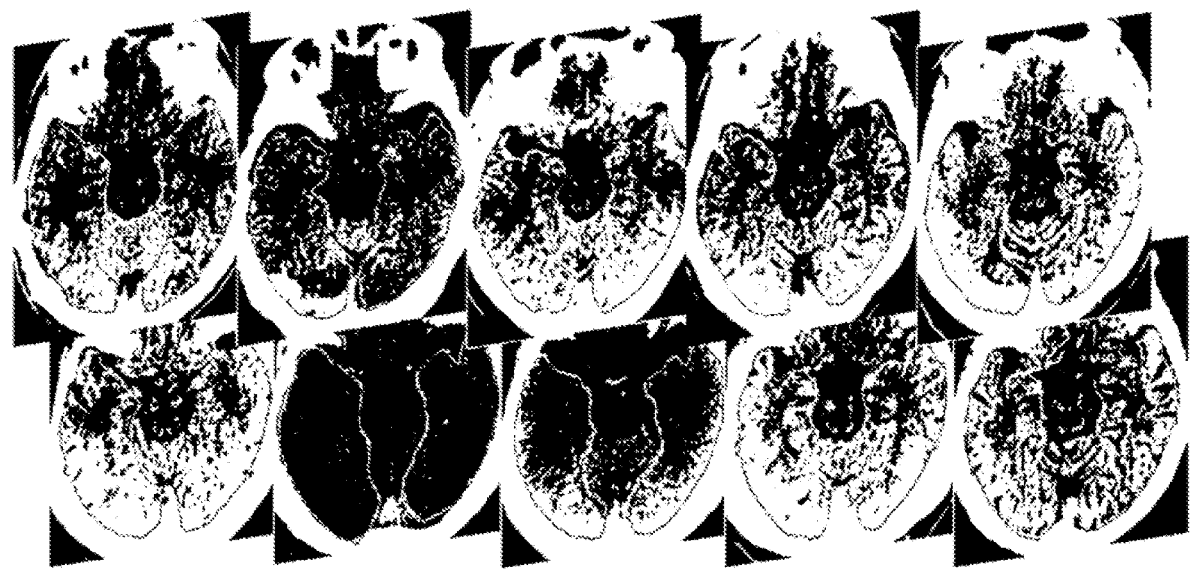
FIGS. 8A-8E are views exemplifying a process of dividing a normalized image by creating a standard mask template in FIG. 7.
Figure 8B:
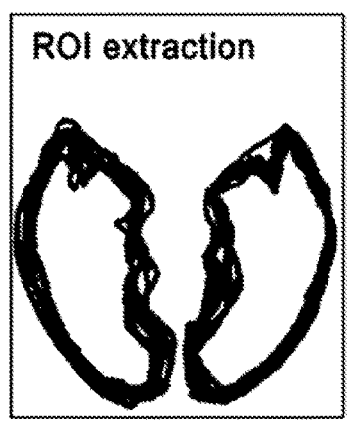
Figure 8C:
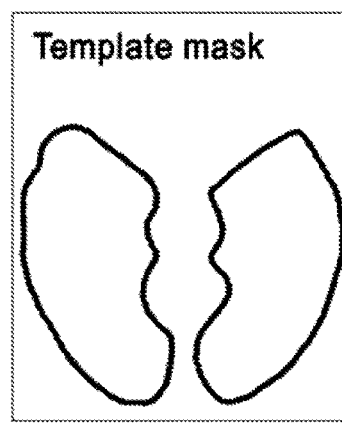
Figure 8D:
Figure 8E:
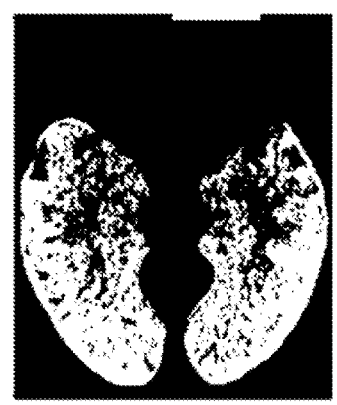

A plurality of medical images is exemplified in FIG. 8A, ROIs extracted from the respective medical images and the set standard mask templates are exemplified in FIGS. 8B and 8C, and normalized medical images and divided and extracted ROIs that are input to medical image processing apparatus, respectively, are exemplified in FIGS. 8D and 8E.

The present disclosure, before dividing and extracting an ROI from a medical image of a diagnosis object, as shown in FIG. 8A, extracts an ROI from a plurality of medical images obtained from a plurality of normal people and patients with brain diseases (FIG. 8B), and creates a standard mask template of the ROI for diagnosing a brain disease of the diagnosis object (FIG. 8C).

The template setter 31 may create a 2D normalization image by setting a voxel in a predetermined unit, for example, in mm about the X-axis, Y-axis, and Z-axis of a 3D normalization image.

Further, the template setter 31 divides an ROI in the created 2D normalization image and creates a standard mask template on the basis of ROIs divided from a plurality of normalization images.

Returning back to FIG. 7, the image normalizer 32 normalizes a medical image of a diagnosis object obtained from the preprocessor 20 (S44).

Figure 9A:
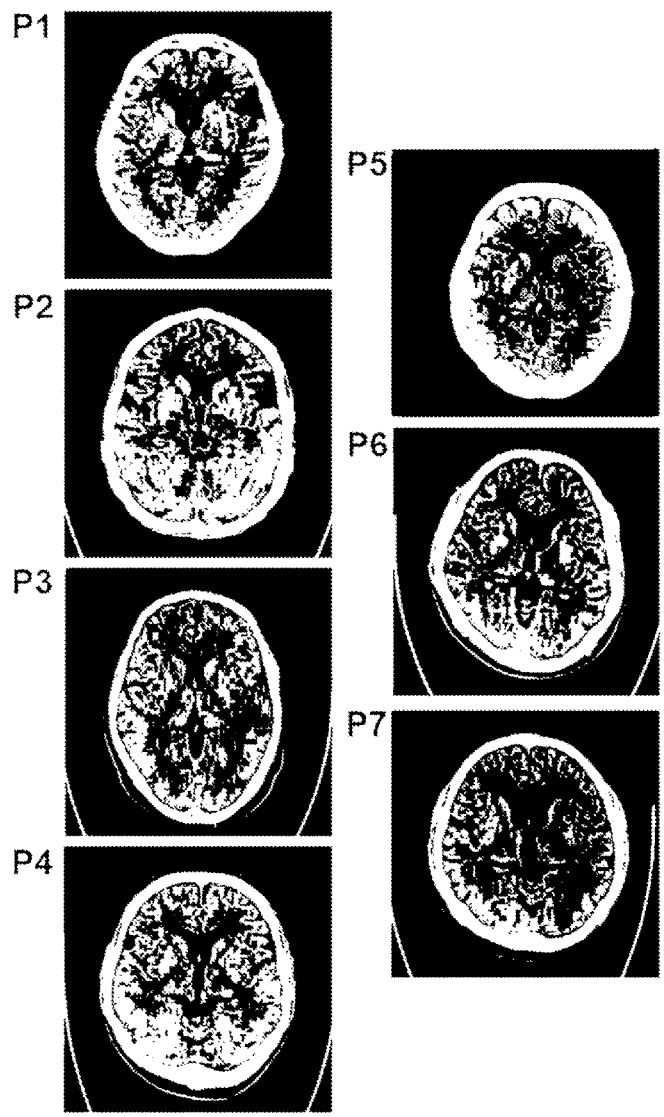
FIGS. 9A-9B are views exemplifying a medical image normalized using the template in FIG. 7.
Figure 9B:
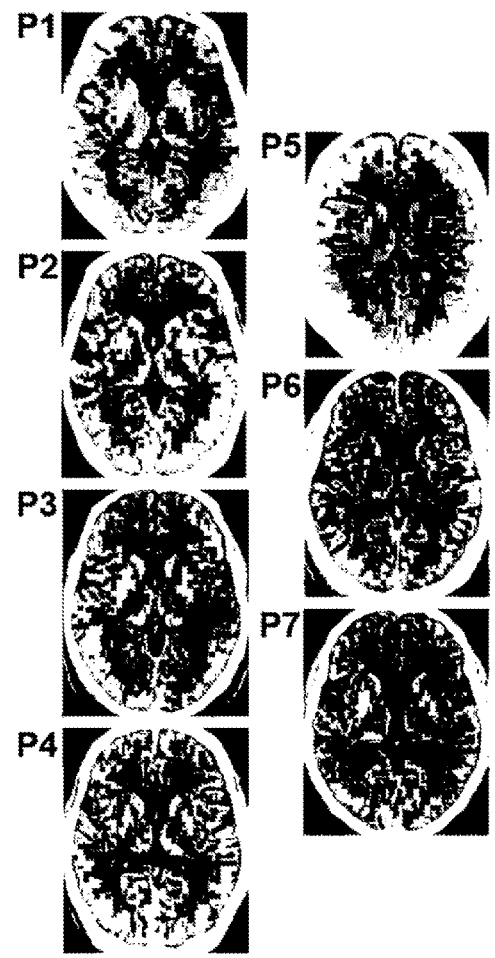

In relation to the step (S44), an original medical image that is input to a medical image processing apparatus is exemplified in FIG. 9A and an image normalized through a template is exemplified in FIG. 9B.

The image normalizer 30 may normalize a medical image, as shown in FIG. 9B, through a process of correcting a non-uniform bias in an original medical image of a diagnosis object shown in FIG. 9A, performing co-registration through spatial alignment, and performing spatial normalization by applying a standard stereotaxic space.

After the step (S44), the ROI extractor 33 divides and extracts only an ROI by applying a standard mask template to the normalized medical image (S45).

That is, the ROI extractor 33 divides and extracts only an ROI, as shown in FIG. 8E, by applying a standard mask template to the normalized medical image shown in FIG. 8D.

In the step (S45), the ROI extractor 33 may divide and extract an ROI by discriminating territories related to Anterior/Middle/Posterior cerebral arteries (ACA, MCA, PCA) and dividing a brain structure related to ACA, MCA, PCA territories in each of the left and right hemispheres.

A medical image including an ROI divided and extracted in this way is transmitted to a brain disease analysis apparatus 13.

Accordingly, the determiner 40 may precisely observe and give a mark to a cerebral region that is vulnerable to cerebral artery damage on the basis of the medical image of the divided and extracted ROI, whereby it is possible to estimate the degree of seriousness and prognosis of a brain disease.

Through the spatial normalization and segmentation step (S40) described above, the present disclosure normalizes a medical image of the brain and divides and extracts a region required for diagnosing a brain disease, that is, an ROI related to cerebral artery damage by applying a preset standard mask template to the normalized medical image, whereby it is possible to consistently divide ROIs from medical images of all examinees on the basis of images normalized through a template. Further, since a brain disease is analyzed and diagnosed through a divided and extracted ROI, precision and accuracy may be maximized.

After the spatial normalization and segmentation step (S40), a process (S50) of classifying ischemia on the basis of the divided and extracted ROI by applying a standard mask template to the normalized medical image is progressed.

Process of Classifying Ischemia

The ischemia classifier 41 determines whether a non-hemorrhage patient has ischemia by receiving an ROI divided and extracted by applying a standard mask template to a normalized medical image by the ROI extractor 33.

Figure 10:
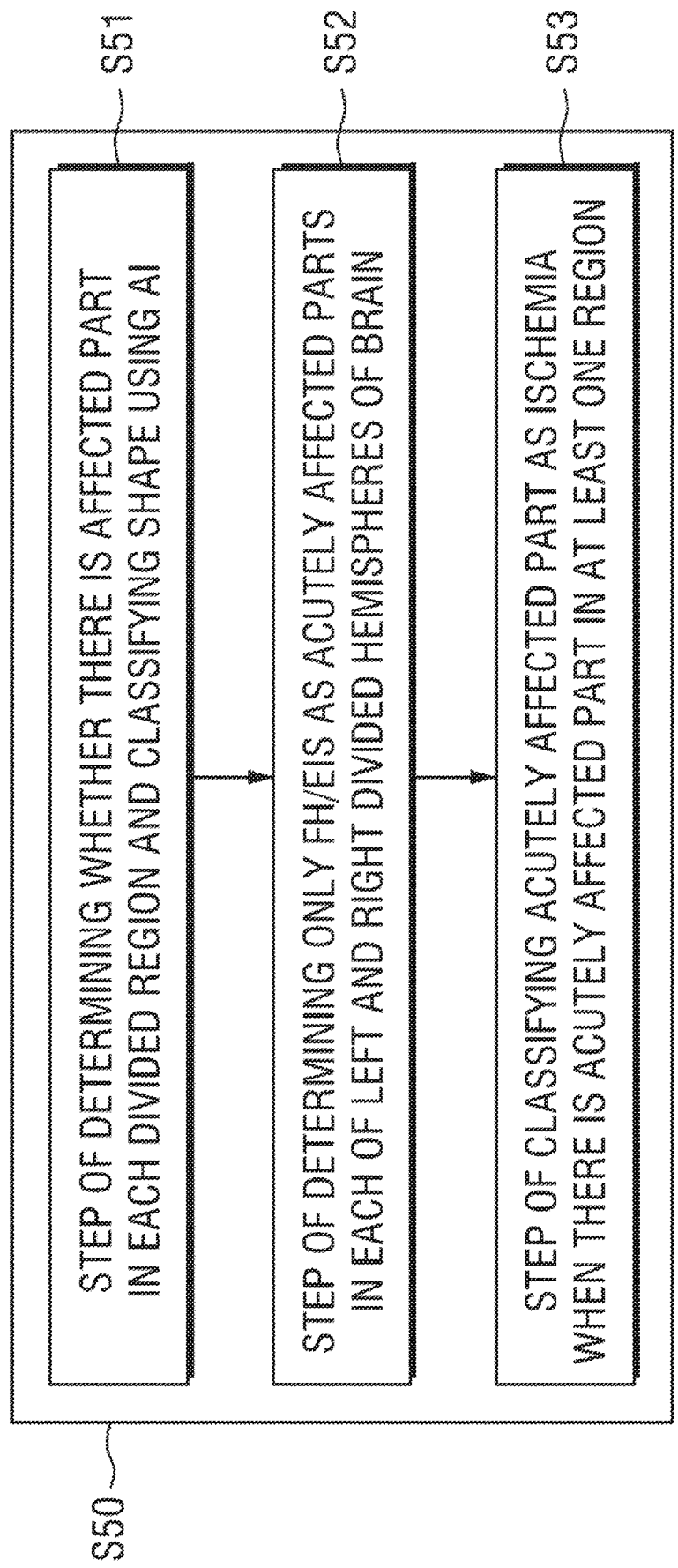
FIG. 10 is a flowchart showing a process of classifying Ischemia in the process described with reference to FIG. 5.

FIG. 10 is a flowchart showing the process (S50) of classifying Ischemia in the process described with reference to FIG. 5.

Referring to FIG. 10, the ischemia classifier 41 according to the present disclosure may use a method of determining whether there is an affected part in a divided region and classifying the shape, using AI.

First, the ischemia classifier 41 according to the present disclosure may independently perform determining whether there is an affected part in each divided region and classifying the shape in relation to Old infarct (OI)/Recent infarct (RI)/Frank hypodensity (FH)/Early ischemic sign (EIS) (S51).

Thereafter, the ischemia classifier 41 determines only FH/EIS as acutely affected parts in each of the divided left and right hemispheres of the brain (S52).

Further, when there is an acutely affected part even in one region, the ischemia classifier 41 determines that a non-hemorrhage patient has ischemia (S53).

If a patient with non-hemorrhage does not have ischemia in the step (S53), a conservative treatment step (S120) is progressed.

Process of Determining Large Vessel Occlusion

Figure 11:
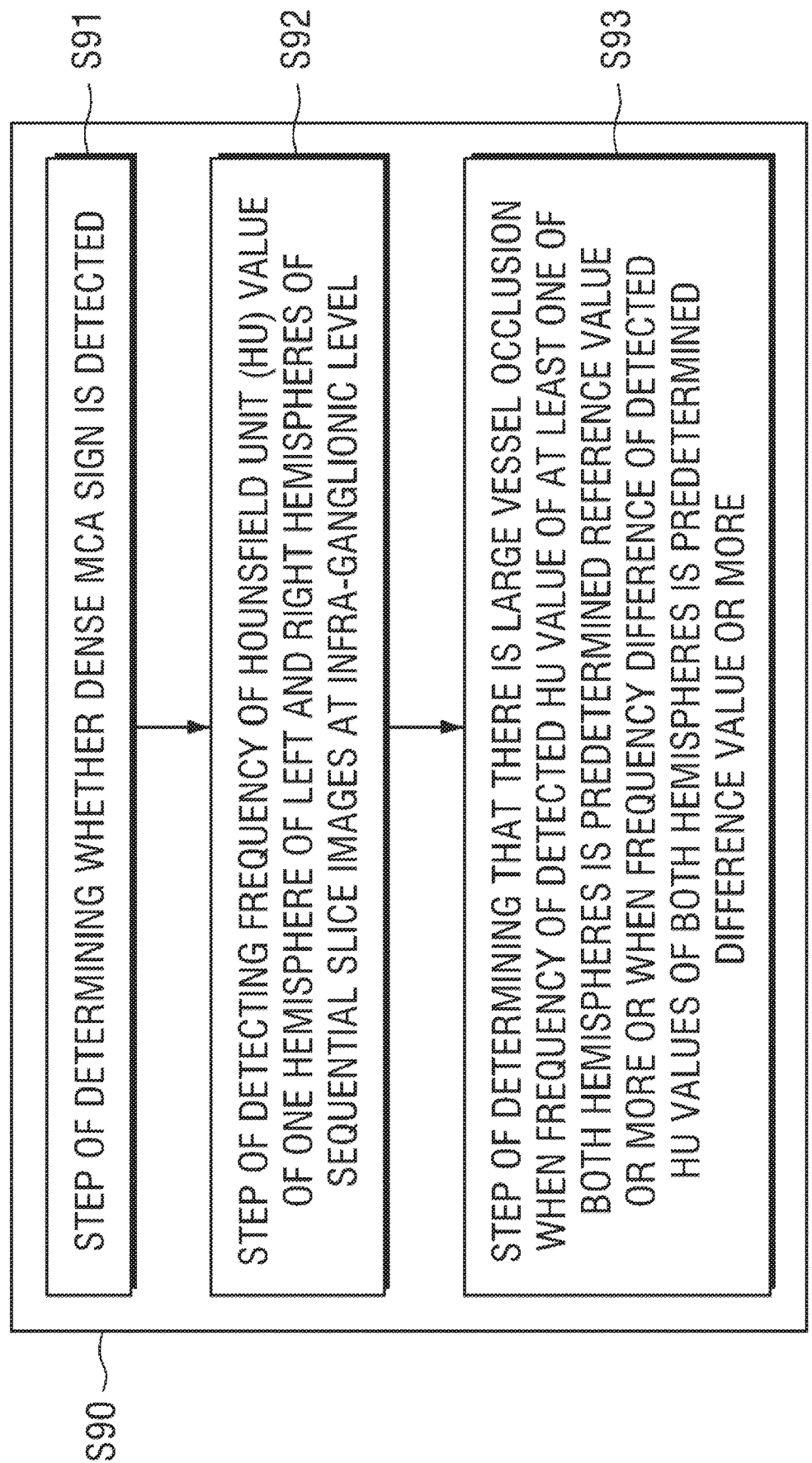
FIG. 11 is a flowchart showing a process of determining large vessel occlusion in the process described with reference to FIG. 5.

FIG. 11 is a flowchart showing a process of determining large vessel occlusion in the process described with reference to FIG. 5.

In a step (S90), first of all, a step of determining whether a dense MCA sign has been detected (S91) is progressed.

If a dense MCA sign is detected, it is considered that large vessel occlusion has been generated.

Meanwhile, even though large vessel occlusion is generated, a case in which a dense MCA sign is not detected may be intermittently generated.

Accordingly, in the present disclosure, even if a dense MCA sign is not detected, the large vessel occlusion determiner 43 derives the frequency difference in Hounsfield unit (HU) values of the left and right hemispheres in sequential slice images at the infra-ganglionic level, thereby being able to make up for the problem.

That is, referring to FIG. 11, the large vessel occlusion determiner 43 detects the frequency of each of the Hounsfield unit (HU) values of one of the left and right hemispheres of sequential slice images at the infra-ganglionic level (S92).

Thereafter, the large vessel occlusion determiner 43 may determine that there is large vessel occlusion when the frequency of the detected HU value of at least one of both hemispheres is a predetermined reference value or more or when the frequency difference of the detected HU values of both hemispheres is a predetermined difference value or more (S93).

If a patient does not have large vessel occlusion, a conservative treatment process (S120) is performed, but when a patient has large vessel occlusion, it is required to determine whether mechanical thrombectomy can be applied to the patient.

In order to determine whether mechanical thrombectomy can be applied to the patient, a step of estimating an ASPECT score (S100) is performed after the step (S90).

Process of Estimating ASPECT Score

The ASPECTS determiner 44 receives an ROI divided and extracted by applying a standard mask template to a normalized medical image by the ROI extractor 33, and calculates an ASPECT score.

Figure 12:
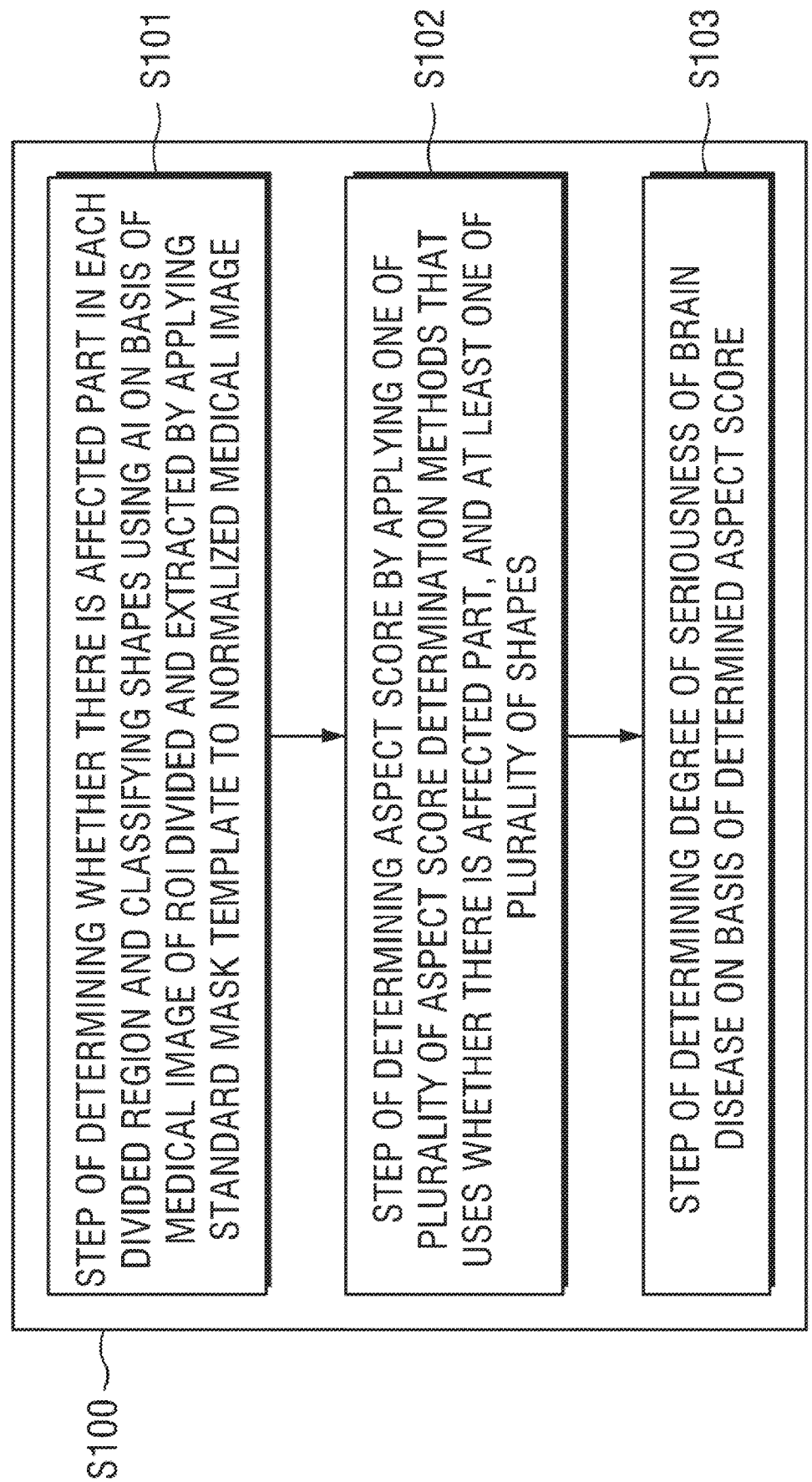
FIG. 12 is a flowchart showing step by step an ASPECT score estimation method in the process described with reference to FIG. 5.

FIG. 12 is a flowchart showing step by step an ASPECT score estimation method in the process described with reference to FIG. 5.

Referring to FIG. 12, the ASPECTS determiner 44 performs a step (S101) of determining whether there is an affected part in each divided region and classifying the shapes using AI on the basis of a medical image of an ROI divided and extracted by applying a standard mask template to a normalized medical image.

In this case, Old infarct (OI)/Recent infarct (RI)/Frank hypodensity (FH)/Early ischemic sign (EIS), etc. may be representative of detection of an affected part and shape classification.

Thereafter, the ASPECTS determiner 44 performs a step (S102) of determining an ASPECT score by applying one of a plurality of ASPECT score determination methods that use whether there is an affected part, and at least one of a plurality of shapes.

In the step (S102), the ASPECTS determiner 44 may calculate an ASPECT score by detecting an affected part and classifying the shape.

In this case, a conventional ASPECTS calculation method that admits as an affected part when even one of OI/RI/FH/EIS is detected by applying an AI algorithm.

Further, in the present invention, a modified ASPECTS calculation method that admits only detection of FH/EIS as an affected part by applying an AI algorithm may be applied.

Further, in the present disclosure, an extended ASPECTS calculation method that adds a region related to ACA, PCA, and ICA and admits only detection of FH/EIS as an affected part by applying an AI algorithm may be applied.

After the step (S102), a step (S103) of determining the degree of seriousness of the brain disease on the basis of the determined ASPECT score is progressed.

After the step (S100), the mechanical thrombectomy determiner 45 determines whether mechanical thrombectomy can be applied to the patient, using the ASPECT score transmitted from the ASPECTS determiner 44 (S110).

Process of Determining Patient with Emergent Large Vessel Occlusion on Basis of AI Algorithm.

In relation to the step (S110), when a patient has large vessel occlusion and a score is lower than a specific reference using the ASPECT score transmitted from the ASPECTS determiner 44, there is little possibility of recovery, so the mechanical thrombectomy determiner 45 determines that mechanical thrombectomy cannot be applied, and progresses a conservative treatment (S120).

However, even if the patient has large vessel occlusion, when the ASPECT score transmitted from the ASPECTS determiner 44 is a predetermined value or more, there is a possibility of recovery, so it is determined that mechanical thrombectomy can be applied to the patient. When it is determined that mechanical thrombectomy can be applied to the patient, various items of information about the patient may be transmitted to a tertiary hospital (S140).

The information that is transmitted to a tertiary hospital may be at least one of an elapsed time, a non-contrast CT image, a determination result and tissue clock information, conventional ASPECTS information, modified ASPECTS information, and extended ASPECTS information.

Hereafter, a detailed method in which the mechanical thrombectomy determiner 45 determines whether mechanical thrombectomy can be applied to the patient using an ASPECT score is described.

First Embodiment

Figure 13:
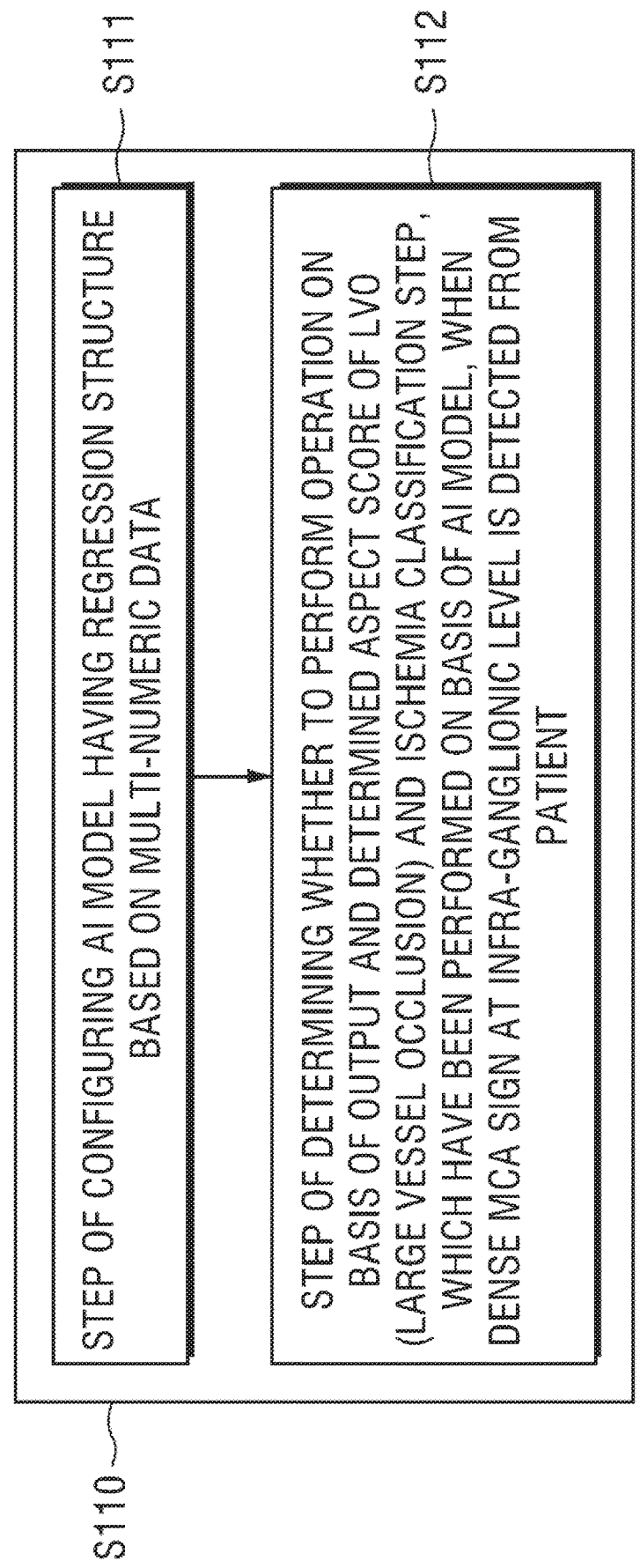
FIG. 13 is a flowchart showing an embodiment that may determine a patient with emergent large vessel occlusion on the basis of an AI algorithm in the process described with reference to FIG. 5.

FIG. 13 is a flowchart showing an embodiment that may determine a patient with emergent large vessel occlusion on the basis of an AI algorithm in the process described with reference to FIG. 5.

Referring to FIG. 13, the mechanical thrombectomy determiner 45 performs a step (S111) of configuring an AI model having a regression structure based on multi-numeric data.

Thereafter, when a dense MCA sign at the infra-ganglionic level is detected from the patient, the mechanical thrombectomy determiner 45 may determine whether to perform an operation on the basis of the outputs of the ELVO (Emergent large vessel occlusion) (S90) and the ischemia classification step (S70), which have been performed on the basis of an AI model, and the ASPECT score determined through the step (S100) (S112).

That is, even if the estimated ASPECT score is a predetermined value or more, the mechanical thrombectomy determiner 45 may determine that the at least one patient is a patient to whom mechanical thrombectomy can be applied, only when a reference determined through the information obtained by the ischemia classifier 41 and the information obtained by the large vessel occlusion determiner is a predetermined reference or more.

Second Embodiment

Figure 14:
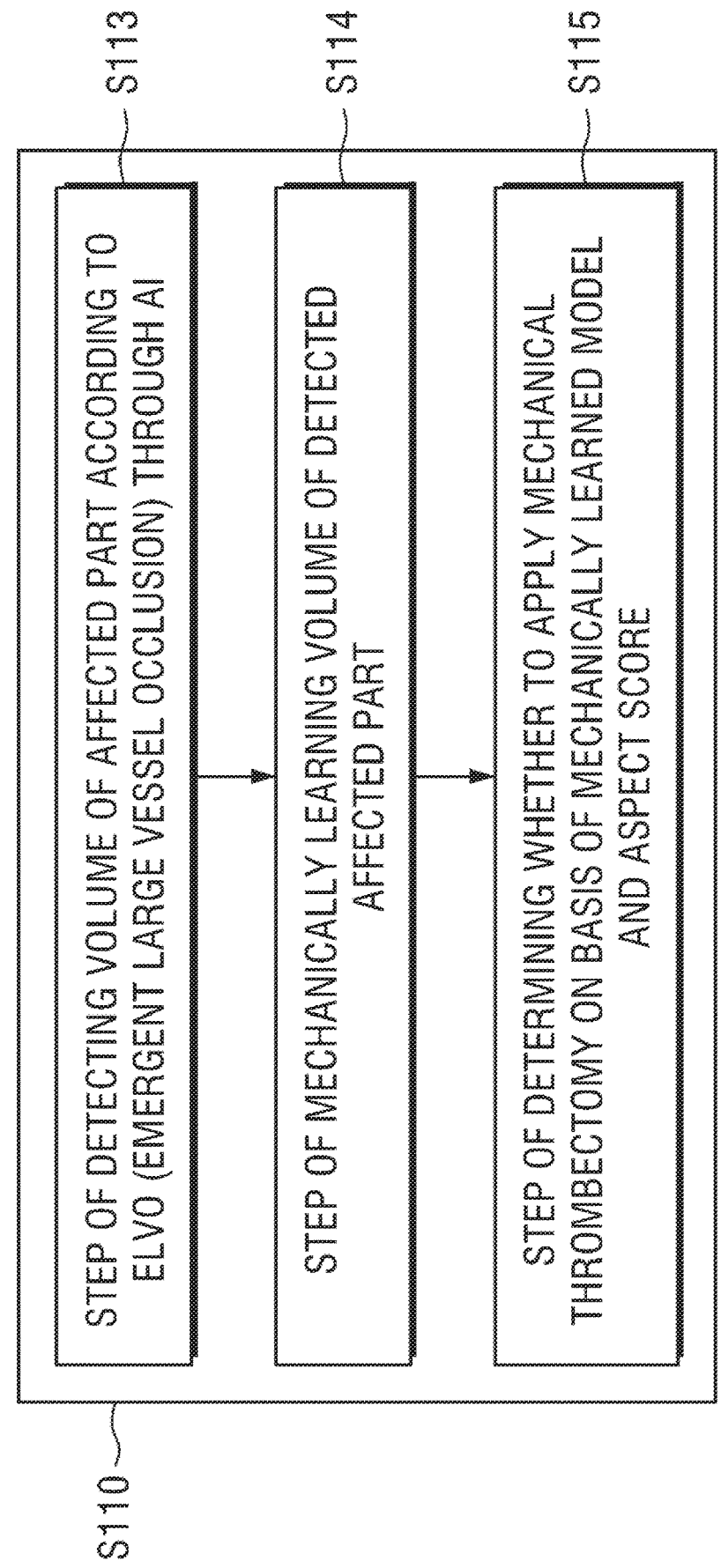
FIG. 14 is a flowchart showing another embodiment that may determine a patient with emergent large vessel occlusion on the basis of an AI algorithm in the process described with reference to FIG. 5.

FIG. 14 is a flowchart showing another embodiment that may determine a patient with emergent large vessel occlusion on the basis of an AI algorithm in the process described with reference to FIG. 5.

Referring to FIG. 14, the mechanical thrombectomy determiner 45 may perform a step (S113) of detecting the volume of an affected part (Early ischemic sign, Frank hypodensity) according to ELVO (Emergent Large Vessel Occlusion) through AI.

Thereafter, the mechanical thrombectomy determiner can perform mechanical learning—logistic regression on the volume of the detected affected part (S114).

Further, the mechanical thrombectomy determiner 45 determines whether to apply mechanical thrombectomy on the basis of the mechanically learned model and the ASPECT score (S115).

That is, it is possible to determine whether the at least one patient is a patient to whom mechanical thrombectomy can be applied, on the basis of an AI model learning the volume value detected due to large vessel occlusion.

Third Embodiment

Figure 15:
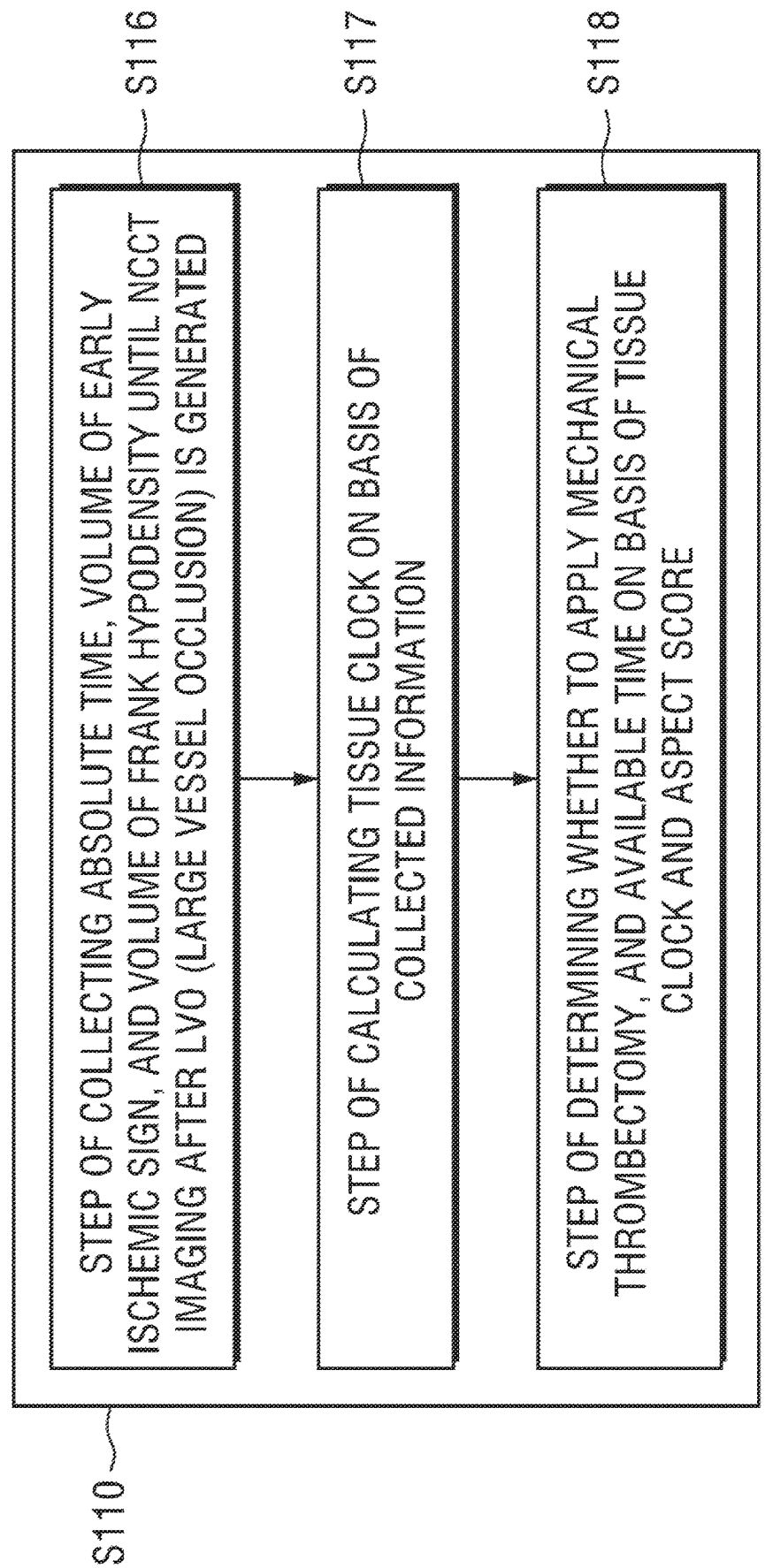
FIG. 15 is a flowchart showing another embodiment that may determine a patient with emergent large vessel occlusion on the basis of an AI algorithm in the process described with reference to FIG. 5.

FIG. 15 is a flowchart showing another embodiment that may determine a patient with emergent large vessel occlusion on the basis of an AI algorithm in the process described with reference to FIG. 5.

Referring to FIG. 15, the mechanical thrombectomy determiner 45 performs a step (S116) of collecting an absolute time and the volumes of early ischemic sign and frank hypodensity until non-contrast CT imaging after LVO (Large Vessel Occlusion) is generated.

Thereafter, the mechanical thrombectomy determiner 45 calculates a tissue clock on the basis of the collected information (S117).

Further, the mechanical thrombectomy determiner 45 determines whether to apply mechanical thrombectomy, and an available time on the basis of the tissue clock and the ASPECT score (S118).

As described above, when it is determined that mechanical thrombectomy can be applied to the patient, various items of information about the patient may be transmitted to a tertiary hospital (S140).

The information that is transmitted to a tertiary hospital may be at least one of an elapsed time, a non-contrast CT image, a determination result and tissue clock information, conventional ASPECTS information, modified ASPECTS information, and extended ASPECTS information.

Method of Increasing Clinical Test Success Possibility by Using Stroke Diagnosis Method Based on AI to Select Patient Group and Normal Group It is possible to increase clinical test success possibility by using the stroke diagnosis method and apparatus according to the present disclosure to select a patient group and a normal group.

That is, the present disclosure may provide an apparatus, a system and a method that may increase the clinical test success possibility using a method of diagnosing a stroke using AI for selecting a patient group and a normal group.

The result of a clinical test for proving the efficacy of a remedy is determined by confirming statistical significance about whether an expected effect estimated in advance is achieved for the participants in the clinical test, and when the stroke diagnosis method and apparatus according to the present disclosure is applied, only patients with a stroke that is accurately aimed by a new medicine are included in clinical test objects, thereby being able to maximally increase the clinical test success possibility.

First, the problems with existing new medicine clinical tests are described.

The result of a clinical test for proving the efficacy of a remedy is determined by confirming statistical significance about whether an expected effect estimated in advance is achieved for the participants in the clinical test.

Meanwhile, as for a stroke, whether the symptom gets better by the efficacy of a remedy should be measured through a medical examination by interview, which has a problem that the index of data is not detailed.

Accordingly, in order to prove statistical significance, the value of an evaluation index should be significantly increased before and after medication or in comparison to a fake medicine group, and as the estimated increasing value is large, the number of target objects decreases and the possibility of achieving statistical significance increases.

In this case, if the estimated increasing value is small, the number of target objects correspondingly increases and the statistic proof difficulty increases.

As a result, it is very difficult to increase the evaluation index of a stroke by one step, so there is a problem that the possibility of the passage of a clinical test is very low.

In the present disclosure, in order to solve this problem, only patients with a stroke that is accurately aimed by a new medicine are included in clinical test objects to maximally increase the clinical test success possibility.

One of important factors of failure in the process of developing a new medicine of central nervous system medicines is that it is difficult to accurately select objects and a medicine reaction group.

Since the central nervous system medicines have a high reaction ratio particularly to placebos, it is an important strategy to decrease heterogeneity in an object group and set a biomarker that may estimate a medicine reactivity in order to increase the success ratio.

Further, since it takes a long time (about 3 months) to confirm a stroke, screening inspection is difficult, so there is a problem that it is very difficult to put only patients with a stroke aimed by a new medicine into the clinical test objects.

Accordingly, it is possible to use the stroke diagnosis method using AI proposed by the present disclosure in order to increase a clinical test success possibility by using the method to select a patient group and a normal group.

FIG. 16 is a view showing a method of increasing a clinical test success possibility using a stroke diagnosis method using artificial intelligence for discriminating a patient group and a normal group.

Referring to FIG. 16, first of all, a step (S1) of recruiting a clinical test examination candidate group for proving the efficacy of a remedy is performed.

Thereafter, the step (S10) in which the image obtainer 10 obtains a non-contrast CT image; the step (S20) in which the preprocessor 20 performs pre-processing and hemorrhage classification; a step in which the hemorrhage classifier 24 learns a hemorrhage type on the basis of AI and discriminates a non-hemorrhage state (S30) and a hemorrhage state (S130) in accordance with an AI algorithm on the basis of a learning model; the spatial normalization and segmentation step (S40) in which it is in the non-hemorrhage state (S30); the process (S50) of classifying ischemia on the basis of the divided and extracted ROI by applying a standard mask template to the normalized medical image; the step (S90) in which the large vessel occlusion determiner 43 determines whether the patient has large vessel occlusion when it is determined that a non-hemorrhage patient has ischemia (S70); the step (S100) of estimating an ASPECT score after the step (S90) in order to determine whether mechanical thrombectomy can be applied to the patient; and the step (S110) in which the mechanical thrombectomy determiner 45 determines whether mechanical thrombectomy can be applied to the patient, using the ASPECT score transmitted from the ASPECTS determiner 44 are performed.

The steps S10 to S110 have been described in detail with reference to FIGS. 5 to 15, so repeated description is omitted to simplify the specification.

After a diagnosis result is derived through the step (S110), a step (S210) of dividing a plurality of examination candidate groups into a group of actual patients with a stroke and a normal patient group may be progressed on the basis of the diagnosis result.

In this case, through a step (S220) of progressing a clinical test on the basis of only the objects classified into the group of actual patients with a stroke and a step (S230) of proving the efficacy of a remedy on the basis of the clinical test result, it is possible to maximally increase the clinical test success possibility by putting the patients with a stroke accurately aimed by a new medicine into clinical test objects.

As a result, it is possible to use the stroke diagnosis method using AI according to the present disclosure in order to increase a clinical test success possibility by using the method to select a patient group and a normal group.

The above-described steps (S1) to (S230) may be independently applied by a stroke diagnosis apparatus 1, or may be applied such that the entire operation is performed by the stroke diagnosis apparatus 1 together with a separate server (not shown) or a separate central management apparatus (not shown).

EFFECT OF PRESENT DISCLOSURE

According to the ASPECT score estimation system and method of the present disclosure, there is an effect that it is possible to estimate an ASPECT score that is an objective index for examining the state of a patient with a stroke using the cerebral CT image of the patient.

Further, according to the present disclosure, there is an effect that it is possible to prevent problems due to scoring variability among specialists and it is possible to use as a reliable index that may make determination of treatment for a patient at a medical site easy, due to the features of a stroke disease that requires quick prescription.

Further, according to the present disclosure, there is an effect that it is possible to overcome inaccuracy of a score value caused by the complexity of the method of estimating an ASPECT score for a stroke through cerebral CT image analysis and the careers of specialists due to the requirement of professionalism.

Further, according to the present disclosure, there is an effect that it is possible to remarkably reduce the manpower and the time and economic costs for an analysis process by automating the entire process of CT image-based stroke analysis.

Further, according to the present disclosure, there is an effect that it is possible to consistently divide and extract a brain region that is vulnerable to cerebral artery damage by normalizing a medical image of a brain such as CT or MRI and applying a preset standard mask template to the normalized medical image.

Further, according to the present disclosure, there is an effect that it is possible to consistently divide and extract an ROI from medical images of all examinees on the basis of a normalized image after normalizing the medical images of diagnosis targets through a template.

As described above, since a brain disease (stroke) is analyzed and diagnosed through an ROI divided and extracted on the basis of a standard mask template, there is an effect that it is possible to maximize precision and accuracy of a diagnosis result.

Further, the result of a clinical examination for proving the efficacy of a remedy is determined by confirming statistical significance about whether an expected effect estimated in advance is achieved for the participants in the clinical examination, and when the stroke diagnosis method and apparatus according to the present disclosure is applied, only patients with a stroke that is accurately aimed by a new medicine are included in clinical examination objects, thereby being able to maximally increase the clinical examination success possibility.

That is, it is possible to use the stroke diagnosis method using AI according to the present disclosure in order to increase a clinical test success possibility by using the method to select a patient group and a normal group.

Meanwhile, the effects of the present disclosure are not limited to the effects described above and other effects may be clearly understood by those skilled in the art from the following description.

The embodiments of the present disclosure described above may be implemented by various means. For example, the embodiments of the present disclosure may be implemented by hardware, firmware, software, or a combination thereof.

When hardware is used, the method according to embodiments of the present disclosure may be implemented by one or more of ASICs (Application Specific Integrated Circuits), DSPs (Digital Signal Processors), DSPDs (Digital Signal Processing Devices), PLDs (Programmable Logic Devices), FPGAs (Field Programmable Gate Arrays), a processor, a controller, a micro controller, a micro processor, and the like.

In the case of an implementation by firmware or software, the method according to the embodiments of the present disclosure may be implemented in the form of a module, a procedure, a function, or the like for performing the functions or operations described above. The software code may be stored in a memory unit and driven by the processor. The memory unit may be located inside or outside the processor, and may exchange data with the processor by various well-known means.

Description of preferred embodiments of the present disclosure described above was provided to enable those skilled in the art to achieve and implement the present disclosure. Although the present disclosure was described above with reference to exemplary embodiments, it should be understood that the present disclosure may be changed and modified in various ways by those skilled in the art, without departing from the scope of the present disclosure. For example, those skilled in the art may combine the components described in the embodiments. Accordingly, the present disclosure is not limited to the embodiments described herein and is intended to provide a widest range coinciding with the principles and new features described herein.

The present disclosure may be implemented in other specific ways without departing from the spirit and necessary features. Accordingly, the detailed description should not be construed as being limited in all respects and should be construed as an example. The scope of the present disclosure should be determined by reasonable analysis of the claims and all changes within an equivalent range of the present disclosure are included in the scope of the present disclosure. The present disclosure is not limited to the embodiments described herein and is intended to provide a widest range coinciding with the principles and new features described herein. Further, unless specifically referred in claims, an embodiment may be configured by combining claims or new claims may be included through amendment after application.

What is claimed is:

1. A stroke diagnosis apparatus based on AI (Artificial Intelligence), the apparatus comprising:
   an image obtainer obtaining a non-contrast CT image related to a brain of at least one patient;

a preprocessor pre-processing the non-contrast CT image and determining whether the at least one patient is in a non-hemorrhage state or a hemorrhage state on the basis of the pre-processed image;

an image processor normalizing the pre-processed image and dividing and extracting an ROI (Region of Interest) using a preset standard mask template; and a determiner determining whether there is a problem with a cerebral large vessel of the at least one patient using the divided and extracted ROI, wherein the determiner estimates an ASPECT score of the at least one patient using the divided and extracted ROI when there is a problem with the cerebral large vessel of the at least one patient, and determines that the at least one patient is a patient to whom mechanical thrombectomy is applied only when the estimated ASPECT score is a predetermined value or more.

2. The stroke diagnosis apparatus according to claim 1, wherein the preprocessor includes:

a noise filter removing noise from the non-contrast CT image;

a register performing co-registration spatially aligning images in objects or between a plurality of objects existing in the non-contrast CT image with the noise removed;

a skull stripper removing portions that are not a brain structure of the at least one patient from the CT image in which the co-registration has been performed; and a hemorrhage classifier determining whether the at least one patient is in a non-hemorrhage state or a hemorrhage state using the CT image in which skull-stripping has been performed.

3. The stroke diagnosis apparatus according to claim 2, wherein when the non-contrast CT image is taken with a gantry inclined, the noise filter performs a tilt correction function that restores an error due to the inclination through re-sampling using gantry tile header information stored together in the original of the non-contrast CT image.

4. The stroke diagnosis apparatus according to claim 2, wherein the register spatially aligns images in the objects or between the plurality of objects existing in the non-contrast CT image that are derived by at least one of inclination or a difference in brain shape due to movement of the at least one patient when the non-contrast CT image is taken.

5. The stroke diagnosis apparatus according to claim 2, wherein the skull stripper removes portions that are not the brain structure in the CT image on the basis of a skull having a relatively higher Hounsfield unit (HU) value than brain tissues.

6. The stroke diagnosis apparatus according to claim 2, wherein the hemorrhage classifier determines whether the at least one patient is in the non-hemorrhage state or the hemorrhage state using the CT image in which the skull-stripping has been performed, on the basis of an A1 model learning cases related to hemorrhage, and the AI model of the hemorrhage classifier is learned using non-contrast CT data of the at least one patient.

7. The stroke diagnosis apparatus according to claim 6, wherein the hemorrhage classifier makes the AI model learn the cases related to the hemorrhage using at least one of Intraparenchymal image, Intraventricular image, Subarachnoid image, Subdural image, and Epidural image in the CT image in which the skull-stripping has been performed.

8. The stroke diagnosis apparatus according to claim 6, wherein the hemorrhage classifier constructs the AI model by configuring a convolutional neural network (CNN) to extract feature maps for each data slice of the non-contrast CT data of the at least one patient, and applying and combining the extracted plurality of feature maps sequentially with a Long Short-term Memory (LSTM) neural network.

9. The stroke diagnosis apparatus according to claim 2, wherein the hemorrhage classifier determines that the at least one patient is in the hemorrhage state when a specific factor exists in over predetermined regions in the CT image in which the skull-stripping has been performed regardless of the hemorrhage classification.

10. The stroke diagnosis apparatus according to claim 1, wherein the image processor includes:

a template setter setting the standard mask template in advance;

an image normalizer normalizing the pre-processed image; and an image processor dividing and extracting the ROI by applying the preset standard mask template to the normalized image;

wherein the image processor operates only when it is determined that the at least one patient is in the non-hemorrhage state.

11. The stroke diagnosis apparatus according to claim 10, wherein the template setter collects a plurality of medical images obtained from a plurality of normal people and patients with brain diseases, creates a 3D normalization image on the basis of the collected images, creates a 2D normalization image by slicing the 3D normalization image based on one axis of an X-axis, a Y-axis, and a Z-axis on the basis of 3D voxels that are predetermined units, and sets the standard mask template in advance on the basis of the ROIs divided from the created 2D normalization image.

12. The stroke diagnosis apparatus according to claim 10, wherein the image normalizer performs the normalization by changing a Hounsfield unit (HU) value of the pre-processed image.

13. The stroke diagnosis apparatus according to claim 1, wherein the determiner includes:

an ischemia classifier determining whether there is ischemia in the brain of the at least one patient using the divided and extracted ROI;

a large vessel occlusion determiner determining whether there is a problem with a cerebral large vessel of the at least one patient when there is the ischemia;

an ASPECTS determiner estimating an ASPECT score of the at least one patient using the divided and extracted ROI when there is a problem with the cerebral large vessel; and a thrombectomy determiner determining that the at least one patient is a patient to whom the mechanical thrombectomy is applied only when the estimated ASPECT score is a predetermined value or more.

14. The stroke diagnosis apparatus according to claim 13, wherein the ischemia classifier determines whether there is the ischemia on the basis of whether there is an affected part in the divided and extracted ROI and an AI model learning shape classification, and the determination of whether there is the affected part in the divided and extracted ROI and the shape classification is performed using Old infarct (OI), Recent infarct (RI), Frank hypodensity (FH), and Early ischemic sign (EIS).

15. The stroke diagnosis apparatus according to claim 14, wherein the ischemia classifier determines that there is the ischemia when there is at least one of the Old infarct (OI), Recent infarct (RI), Frank hypodensity (FH), and Early ischemic sign (EIS) in any one region of the divided and extracted ROIs.

16. The stroke diagnosis apparatus according to claim 13, wherein the problem with the cerebral large vessel is large vessel occlusion, and
the large vessel occlusion determiner determines whether there is a possibility of the large vessel occlusion on the basis of whether a dense MCA sign has been detected at an infra-ganglionic level in relation to the divided and extracted ROI.

17. The stroke diagnosis apparatus according to claim 16, wherein when the dense MCA sign is not detected, the large vessel occlusion determiner detects a frequency of each Hounsfield unit (HU) value in both left and right hemispheres of sequential slice images at the infra-ganglionic level in relation to the divided and extracted ROI, and determines that there is the large vessel occlusion when the frequency of the detected HU values of at least one of the both hemispheres is a predetermined reference value or more or when a frequency difference of the detected HU values of the both hemispheres is a predetermined difference value or more.

18. The stroke diagnosis apparatus according to claim 13, wherein the ASPECTS determiner estimates the ASPECT score on the basis of whether there is the affected part in the divided and extracted ROI and an AI model learning shape classification, and
the determination of whether there is the affected part in the divided and extracted ROI and the shape classification is performed using Old infarct (OI), Recent infarct (RI), Frank hypodensity (FH), and Early ischemic sign (EIS).

19. The stroke diagnosis apparatus according to claim 18, wherein when at least one of the Old infarct (OI), Recent infarct (RI), Frank hypodensity (FH), and Early ischemic sign (EIS) is detected, the ASPECTS determiner admits it as the affected part and reflects the value admitted as the affected part to the estimation of the ASPECT score.

20. The stroke diagnosis apparatus according to claim 18, wherein when the Frank hypodensity (FH) and Early ischemic sign (EIS) of the Old infarct (OI), Recent infarct (RI), Frank hypodensity (FH), and Early ischemic sign (EIS) are detected, the ASPECTS determiner admits them as the affected part and reflects the value admitted as the affected part to the estimation of the ASPECT score.

21. The stroke diagnosis apparatus according to claim 18, wherein the divided and extracted ROI includes an MCA (Middle cerebral artery), ACA (Anterior cerebral artery), PCA (Posterior cerebral artery), and ICA (Internal carotid artery) regions, and when the Frank hypodensity (FH) and the Early ischemic sign (EIS) of the Old infarct (OI), Recent infarct (RI), Frank hypodensity (FH), and Early ischemic sign (EIS) are detected in the MCA, ACA, PCA, and ICA regions, and
the ASPECTS determiner admits them as the affected part and reflects the values admitted as the affected parts to the estimation of the ASPECT score.

22. The stroke diagnosis apparatus according to claim 13, wherein, when the estimated ASPECT score is a predetermined value or more, the thrombectomy determiner determines that the at least one patient is a patient to whom the mechanical thrombectomy is applied, only when a reference determined through information obtained by the ischemia classifier and information obtained by the large vessel occlusion determiner is a predetermined reference or more.

23. The stroke diagnosis apparatus according to claim 13, wherein the thrombectomy determiner determines whether the at least one patient is a patient to whom the mechanical thrombectomy is applied, on the basis of an AI model learning a volume value detected due to a problem with the cerebral large vessel.

24. The stroke diagnosis apparatus according to claim 13, wherein the thrombectomy determiner calculates a tissue clock using an absolute time, the volume of Early ischemic sign (EIS), and the volume of Frank hypodensity (FH) until the non-contrast CT imaging after a problem with the cerebral large vessel is generated, and determines whether the at least one patient is a patient to whom the mechanical thrombectomy is applied, on the basis of the calculated tissue clock.

25. The stroke diagnosis apparatus according to claim 1, further comprising a communication unit transmitting information about the at least one patient to a pre-designated outside when the at least one patient is a patient to whom the mechanical thrombectomy is applied.

26. The stroke diagnosis apparatus according to claim 25, the information that is transmitted to the outside includes elapsed time information, non-contrast CT image information, determination result information, tissue clock information, and the estimated ASPECT score information that are related to the at least one patient.

* * * * *